(12) United States Patent
Slivka et al.

(10) Patent No.: US 10,624,758 B2
(45) Date of Patent: Apr. 21, 2020

(54) ZERO PROFILE SPINAL FUSION CAGE

(71) Applicant: DePuy Synthes Products, Inc., Raynham, MA (US)

(72) Inventors: Michael A. Slivka, Berkley, MA (US); Alexander Grinberg, Auburndale, MA (US); John C. Voellmicke, Franklin, MA (US); John Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 131 days.

(21) Appl. No.: 15/361,678

(22) Filed: Nov. 28, 2016

(65) Prior Publication Data
US 2017/0071756 A1    Mar. 16, 2017

Related U.S. Application Data

(63) Continuation of application No. 12/414,532, filed on Mar. 30, 2009, now Pat. No. 9,526,620.

(51) Int. Cl.
*A61F 2/44* (2006.01)
*A61F 2/30* (2006.01)
*A61F 2/46* (2006.01)

(52) U.S. Cl.
CPC .............. *A61F 2/4455* (2013.01); *A61F 2/44* (2013.01); *A61F 2/442* (2013.01); *A61F 2/447* (2013.01); *A61F 2/4465* (2013.01); *A61F 2/4611* (2013.01); *A61F 2/4684* (2013.01); *A61F 2/30965* (2013.01); *A61F 2/446* (2013.01); *A61F 2/4425* (2013.01); *A61F 2002/30062* (2013.01); *A61F 2002/30596* (2013.01); *A61F 2002/30604* (2013.01); (Continued)

(58) Field of Classification Search
CPC .................. A61B 17/809; A61B 17/86; A61B 2017/00407; A61F 2002/30387; A61F 2/4611; A61F 2/44; A61F 2/4455; A61F 2/442; A61F 2002/4445; A61F 2/4465; A61F 2/447
See application file for complete search history.

(56) References Cited

U.S. PATENT DOCUMENTS 1,636,636 A    7/1927  Humble
1,677,337 A    7/1928  Grove
(Continued)

FOREIGN PATENT DOCUMENTS

CN    201244104 Y    5/2009
CN    101909548 A    12/2010
(Continued)

OTHER PUBLICATIONS

Vandorpe et al in the Handbook of Biodegradable Polymers, edited by Domb et al., Hardwood Academic Press, pp. 161-182, 1997.
(Continued)

*Primary Examiner* — Seema Mathew
(74) *Attorney, Agent, or Firm* — BakerHostetler

(57) ABSTRACT

An interbody fusion cage having upper and lower canals for receiving the heads of bone screws that have been pre-installed in opposing vertebral body endplates. The proximal wall of the cage preferably has a vertical slot that communicates with each canal and is adapted to allow access by a screwdriver and tightening of the screws.

20 Claims, 15 Drawing Sheets

(52) U.S. Cl.
CPC ............... *A61F 2002/30794* (2013.01); *A61F 2002/443* (2013.01); *A61F 2002/4475* (2013.01); *A61F 2002/4622* (2013.01); *A61F 2002/4627* (2013.01); *A61F 2002/4628* (2013.01); *A61F 2210/0004* (2013.01); *A61F 2310/00017* (2013.01); *A61F 2310/00023* (2013.01); *A61F 2310/00029* (2013.01); *A61F 2310/00059* (2013.01); *A61F 2310/00161* (2013.01); *A61F 2310/00203* (2013.01); *A61F 2310/00239* (2013.01); *A61F 2310/00293* (2013.01)

(56) References Cited

U.S. PATENT DOCUMENTS

| | | |
|---|---|---|
| 2,304,703 A | 12/1942 | O'Leary |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Jamiolkowski et al. |
| 4,208,511 A | 6/1980 | Jamiolkowski et al. |
| 4,349,921 A | 9/1982 | Kuntz |
| 4,743,256 A | 5/1988 | Brantigan |
| 4,863,476 A | 9/1989 | Shepperd |
| 4,904,261 A | 2/1990 | Dove et al. |
| 4,955,908 A | 9/1990 | Frey et al. |
| 5,041,113 A | 8/1991 | Biedermann et al. |
| 5,059,193 A | 10/1991 | Kuslich |
| 5,123,926 A | 6/1992 | Pisharodi |
| 5,147,361 A | 9/1992 | Ojima et al. |
| 5,209,751 A | 5/1993 | Farris et al. |
| 5,290,312 A | 3/1994 | Kojimoto et al. |
| 5,306,308 A | 4/1994 | Gross et al. |
| 5,344,252 A | 9/1994 | Kakimoto |
| 5,352,231 A | 10/1994 | Brumfield et al. |
| 5,370,697 A | 12/1994 | Baumgartner |
| 5,390,683 A | 2/1995 | Pisharodi |
| 5,391,170 A | 2/1995 | McGuire et al. |
| 5,395,372 A | 3/1995 | Holt et al. |
| 5,397,364 A | 3/1995 | Kozak et al. |
| 5,443,514 A | 8/1995 | Steffee |
| 5,443,515 A | 8/1995 | Cohen et al. |
| 5,464,407 A | 11/1995 | McGuire |
| 5,464,929 A | 11/1995 | Bezwada et al. |
| 5,499,986 A | 3/1996 | Dimarco |
| 5,522,899 A | 6/1996 | Michelson |
| 5,529,580 A | 6/1996 | Kusunoki et al. |
| 5,534,029 A | 7/1996 | Shima |
| 5,534,031 A | 7/1996 | Matsuzaki et al. |
| 5,554,191 A | 9/1996 | Lahille et al. |
| 5,578,034 A | 11/1996 | Estes |
| 5,591,166 A | 1/1997 | Bernhardt et al. |
| 5,595,751 A | 1/1997 | Bezwada et al. |
| 5,597,579 A | 1/1997 | Bezwada et al. |
| 5,601,553 A | 2/1997 | Trebing et al. |
| 5,607,687 A | 3/1997 | Bezwada et al. |
| 5,609,635 A | 3/1997 | Michelson |
| 5,609,636 A | 3/1997 | Kohrs et al. |
| 5,618,552 A | 4/1997 | Bezwada et al. |
| 5,620,458 A | 4/1997 | Green et al. |
| 5,620,698 A | 4/1997 | Bezwada et al. |
| 5,645,598 A | 7/1997 | Brosnahan, III |
| 5,645,850 A | 7/1997 | Bezwada et al. |
| 5,648,088 A | 7/1997 | Bezwada et al. |
| 5,653,763 A | 8/1997 | Errico et al. |
| 5,658,335 A | 8/1997 | Allen |
| 5,662,655 A | 9/1997 | Laboureau et al. |
| 5,665,122 A | 9/1997 | Kambin |
| 5,676,666 A | 10/1997 | Oxland et al. |
| 5,697,977 A | 12/1997 | Pisharodi |
| 5,698,213 A | 12/1997 | Jamiolkowski et al. |
| 5,700,583 A | 12/1997 | Jamiolkowski et al. |
| 5,713,899 A | 2/1998 | Marnay et al. |
| 5,716,415 A | 2/1998 | Steffee |
| 5,755,796 A | 5/1998 | Ibo et al. |
| 5,772,661 A | 6/1998 | Michelson |
| 5,776,196 A | 7/1998 | Matsuzaki et al. |
| 5,779,707 A | 7/1998 | Bertholet et al. |
| 5,782,832 A | 7/1998 | Larsen et al. |
| 5,785,713 A | 7/1998 | Jobe |
| 5,788,698 A | 8/1998 | Savornin |
| 5,797,912 A | 8/1998 | Runciman et al. |
| 5,797,918 A | 8/1998 | McGuire et al. |
| 5,800,435 A | 9/1998 | Errico et al. |
| 5,800,440 A | 9/1998 | Stead |
| 5,859,150 A | 1/1999 | Jamiolkowski et al. |
| 5,860,973 A | 1/1999 | Michelson |
| 5,865,848 A | 2/1999 | Baker |
| 5,888,223 A | 3/1999 | Bray, Jr. |
| 5,888,224 A | 3/1999 | Beckers et al. |
| 5,893,889 A | 4/1999 | Harrington |
| 5,893,890 A | 4/1999 | Pisharodi |
| 5,904,689 A | 5/1999 | Jonjic |
| 5,913,860 A | 6/1999 | Scholl |
| 5,980,522 A | 11/1999 | Koros et al. |
| 6,039,761 A | 3/2000 | Li et al. |
| 6,045,579 A | 4/2000 | Hochschuler et al. |
| 6,049,026 A | 4/2000 | Muschler |
| 6,056,749 A | 5/2000 | Kuslich |
| 6,066,175 A | 5/2000 | Henderson et al. |
| 6,086,593 A | 7/2000 | Bonutti |
| 6,093,205 A | 7/2000 | McLeod et al. |
| 6,099,531 A | 8/2000 | Bonutti |
| 6,102,950 A | 8/2000 | Vaccaro |
| 6,106,557 A | 8/2000 | Robioneck et al. |
| 6,117,174 A | 9/2000 | Nolan |
| 6,120,503 A | 9/2000 | Michelson |
| 6,126,689 A | 10/2000 | Brett |
| 6,127,597 A | 10/2000 | Beyar et al. |
| 6,129,763 A | 10/2000 | Chauvin et al. |
| 6,139,550 A | 10/2000 | Michelson |
| 6,146,387 A | 11/2000 | Trott et al. |
| 6,156,037 A | 12/2000 | Lehuec et al. |
| 6,159,211 A | 12/2000 | Boriani et al. |
| 6,159,244 A | 12/2000 | Suddaby |
| 6,174,311 B1 | 1/2001 | Branch et al. |
| 6,176,882 B1 | 1/2001 | Biedermann et al. |
| 6,179,794 B1 | 1/2001 | Burras |
| 6,179,873 B1 | 1/2001 | Zientek |
| 6,179,875 B1 | 1/2001 | Von Strempel |
| 6,183,517 B1 | 2/2001 | Suddaby |
| 6,190,414 B1 | 2/2001 | Young et al. |
| 6,193,757 B1 | 2/2001 | Foley et al. |
| 6,200,306 B1 | 3/2001 | Klostermeyer et al. |
| 6,206,922 B1 | 3/2001 | Zdeblick et al. |
| 6,224,602 B1 | 5/2001 | Hayes |
| 6,231,610 B1 | 5/2001 | Geisler |
| 6,235,059 B1 | 5/2001 | Benezech et al. |
| 6,296,647 B1 | 10/2001 | Robioneck et al. |
| 6,302,914 B1 | 10/2001 | Michelson |
| 6,306,170 B2 | 10/2001 | Ray |
| 6,330,845 B1 | 12/2001 | Meulink |
| 6,332,895 B1 | 12/2001 | Suddaby |
| 6,336,928 B1 | 1/2002 | Guerin et al. |
| 6,342,055 B1 | 1/2002 | Eisermann et al. |
| 6,342,074 B1 | 1/2002 | Simpson |
| 6,364,880 B1 | 4/2002 | Michelson |
| 6,368,351 B1 | 4/2002 | Glenn et al. |
| 6,375,462 B2 | 4/2002 | Holweg et al. |
| 6,375,682 B1 | 4/2002 | Fleischmann et al. |
| 6,387,130 B1 | 5/2002 | Stone et al. |
| 6,395,031 B1 | 5/2002 | Foley et al. |
| 6,406,478 B1 | 6/2002 | Kuo |
| 6,409,766 B1 | 6/2002 | Brett |
| 6,413,278 B1 | 7/2002 | Marchosky |
| 6,419,705 B1 | 7/2002 | Erickson |
| 6,419,706 B1 | 7/2002 | Graf |
| 6,423,063 B1 | 7/2002 | Bonutti |
| 6,428,575 B2 | 8/2002 | Koo et al. |
| 6,432,106 B1 | 8/2002 | Fraser |
| 6,436,140 B1 | 8/2002 | Liu et al. |
| 6,447,544 B1 | 9/2002 | Michelson |

(56) References Cited

U.S. PATENT DOCUMENTS

| | | |
|---|---|---|
| 6,447,546 B1 | 9/2002 | Bramlet et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,461,359 B1 * | 10/2002 | Tribus .............. A61B 17/7059 606/247 |
| 6,471,724 B2 | 10/2002 | Zdeblick et al. |
| 6,488,710 B2 | 12/2002 | Besselink |
| 6,508,818 B2 | 1/2003 | Steiner et al. |
| 6,527,804 B1 | 3/2003 | Gauchet et al. |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett et al. |
| 6,572,619 B2 | 6/2003 | Santilli |
| 6,579,290 B1 | 6/2003 | Hardcastle et al. |
| 6,582,468 B1 | 6/2003 | Gauchet |
| 6,602,257 B1 | 8/2003 | Thramann |
| 6,610,094 B2 | 8/2003 | Husson |
| 6,629,998 B1 | 10/2003 | Lin |
| 6,641,614 B1 | 11/2003 | Wagner et al. |
| 6,648,917 B2 | 11/2003 | Gerbec et al. |
| 6,672,977 B1 | 1/2004 | Colbo et al. |
| 6,676,665 B2 | 1/2004 | Foley et al. |
| 6,682,563 B2 | 1/2004 | Scharf |
| 6,695,846 B2 | 2/2004 | Richelsoph et al. |
| 6,706,070 B1 | 3/2004 | Wagner et al. |
| 6,719,796 B2 | 4/2004 | Cohen et al. |
| 6,723,126 B1 | 4/2004 | Berry |
| 6,730,125 B1 | 5/2004 | Lin |
| 6,730,127 B2 | 5/2004 | Michelson |
| 6,733,531 B1 | 5/2004 | Trieu |
| 6,733,532 B1 | 5/2004 | Gauchet et al. |
| 6,736,850 B2 | 5/2004 | Davis |
| 6,743,255 B2 | 6/2004 | Ferree |
| 6,743,257 B2 | 6/2004 | Castro |
| 6,745,255 B2 | 6/2004 | Yen et al. |
| 6,761,738 B1 | 7/2004 | Boyd |
| 6,770,096 B2 | 8/2004 | Bolger et al. |
| 6,773,437 B2 | 8/2004 | Ogilvie et al. |
| 6,776,781 B1 | 8/2004 | Uwaydah |
| 6,805,714 B2 | 10/2004 | Sutcliffe |
| 6,808,537 B2 | 10/2004 | Michelson |
| 6,824,564 B2 | 11/2004 | Crozet |
| 6,824,565 B2 | 11/2004 | Muhanna et al. |
| 6,833,006 B2 | 12/2004 | Foley et al. |
| 6,835,208 B2 | 12/2004 | Marchosky |
| 6,837,905 B1 | 1/2005 | Lieberman |
| 6,849,093 B2 | 2/2005 | Michelson |
| 6,855,167 B2 | 2/2005 | Shimp et al. |
| 6,863,673 B2 | 3/2005 | Gerbec et al. |
| 6,890,335 B2 | 5/2005 | Grabowski et al. |
| 6,890,355 B2 | 5/2005 | Michelson |
| 6,893,464 B2 | 5/2005 | Kiester |
| 6,945,973 B2 | 9/2005 | Bray |
| 6,953,477 B2 | 10/2005 | Berry |
| 6,955,691 B2 | 10/2005 | Chae et al. |
| 6,969,404 B2 | 11/2005 | Ferree |
| 6,969,405 B2 | 11/2005 | Suddaby |
| 6,972,019 B2 | 12/2005 | Michelson |
| 6,974,479 B2 | 12/2005 | Trieu |
| 6,974,480 B2 | 12/2005 | Messerli et al. |
| 6,984,234 B2 | 1/2006 | Bray |
| 7,001,385 B2 | 2/2006 | Bonutti |
| 7,018,412 B2 | 3/2006 | Ferreira et al. |
| 7,018,416 B2 | 3/2006 | Hanson et al. |
| 7,033,394 B2 | 4/2006 | Michelson |
| 7,037,339 B2 | 5/2006 | Houfburg |
| 7,041,135 B2 | 5/2006 | Michelson |
| 7,044,971 B2 | 5/2006 | Suddaby |
| 7,056,341 B2 | 6/2006 | Crozet |
| 7,063,491 B2 | 6/2006 | French |
| 7,070,598 B2 | 7/2006 | Lim et al. |
| 7,077,864 B2 | 7/2006 | Byrd et al. |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,163,561 B2 | 1/2007 | Michelson |
| 7,172,627 B2 | 2/2007 | Fiere et al. |
| 7,211,112 B2 | 5/2007 | Baynham et al. |
| 7,217,293 B2 | 5/2007 | Branch, Jr. |
| 7,220,280 B2 | 5/2007 | Kast et al. |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,232,463 B2 | 6/2007 | Falahee |
| 7,232,464 B2 | 6/2007 | Mathieu et al. |
| 7,235,101 B2 | 6/2007 | Berry et al. |
| 7,238,203 B2 | 7/2007 | Bagga et al. |
| 7,238,206 B2 | 7/2007 | Lange et al. |
| 7,255,698 B2 | 8/2007 | Michelson |
| 7,276,081 B1 | 10/2007 | Coates et al. |
| 7,288,094 B2 | 10/2007 | Lindemann et al. |
| 7,288,095 B2 | 10/2007 | Baynham et al. |
| 7,288,114 B2 | 10/2007 | Lange |
| 7,306,605 B2 | 12/2007 | Ross |
| 7,309,358 B2 | 12/2007 | Berry et al. |
| 7,311,734 B2 | 12/2007 | Van et al. |
| 7,316,714 B2 | 1/2008 | Gordon et al. |
| 7,318,839 B2 | 1/2008 | Malberg et al. |
| 7,323,011 B2 | 1/2008 | Shepard et al. |
| 7,326,248 B2 | 2/2008 | Michelson |
| 7,332,209 B2 | 2/2008 | Yokouchi et al. |
| 7,338,525 B2 | 3/2008 | Ferree |
| 7,341,587 B2 | 3/2008 | Molz et al. |
| 7,341,590 B2 | 3/2008 | Ferree |
| 7,354,452 B2 | 4/2008 | Foley |
| 7,361,193 B2 | 4/2008 | Frey et al. |
| 7,435,262 B2 | 10/2008 | Michelson |
| 7,438,715 B2 | 10/2008 | Doubler et al. |
| 7,442,209 B2 | 10/2008 | Michelson |
| 7,452,370 B2 | 11/2008 | Anderson |
| 7,491,237 B2 | 2/2009 | Randall et al. |
| 7,503,933 B2 | 3/2009 | Michelson |
| 7,507,241 B2 | 3/2009 | Levy et al. |
| 7,513,900 B2 | 4/2009 | Carrison et al. |
| 7,527,641 B2 | 5/2009 | Suh |
| 7,569,074 B2 | 8/2009 | Eisermann et al. |
| 7,594,931 B2 | 9/2009 | Louis et al. |
| 7,594,932 B2 | 9/2009 | Aferzon et al. |
| 7,601,171 B2 | 10/2009 | Ainsworth et al. |
| 7,601,173 B2 | 10/2009 | Messerli et al. |
| 7,608,062 B2 | 10/2009 | Sweeney |
| 7,618,456 B2 | 11/2009 | Mathieu et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,628,816 B2 | 12/2009 | Magerl et al. |
| 7,641,665 B2 | 1/2010 | Zubok et al. |
| 7,655,042 B2 | 2/2010 | Foley et al. |
| 7,658,766 B2 | 2/2010 | Melkent et al. |
| 7,662,182 B2 | 2/2010 | Zubok et al. |
| 7,674,279 B2 | 3/2010 | Johnson |
| 7,691,147 B2 | 4/2010 | Guetlin et al. |
| 7,703,727 B2 | 4/2010 | Selness |
| 7,704,255 B2 | 4/2010 | Michelson |
| 7,722,612 B2 | 5/2010 | Sala et al. |
| 7,722,674 B1 | 5/2010 | Grotz |
| 7,726,002 B2 | 6/2010 | Shimp et al. |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,794,502 B2 | 9/2010 | Michelson |
| 7,815,643 B2 | 10/2010 | Johnson et al. |
| 7,815,681 B2 | 10/2010 | Ferguson |
| 7,819,921 B2 | 10/2010 | Grotz |
| 7,824,445 B2 | 11/2010 | Biro et al. |

(56) References Cited

U.S. PATENT DOCUMENTS

| | | | |
|---|---|---|---|
| 7,837,734 | B2 | 11/2010 | Zucherman et al. |
| 7,846,106 | B2 | 12/2010 | Andrews et al. |
| 7,846,206 | B2 | 12/2010 | Oglaza et al. |
| 7,846,207 | B2 | 12/2010 | Lechmann et al. |
| 7,846,210 | B2 | 12/2010 | Perez-Cruet et al. |
| 7,850,733 | B2 | 12/2010 | Baynham et al. |
| 7,854,766 | B2 | 12/2010 | Moskowitz et al. |
| 7,862,616 | B2 | 1/2011 | Lechmann et al. |
| 7,871,441 | B2 | 1/2011 | Eckman |
| 7,874,980 | B2 | 1/2011 | Sonnenschein et al. |
| 7,875,062 | B2 | 1/2011 | Lindemann et al. |
| 7,875,076 | B2 | 1/2011 | Mathieu et al. |
| 7,879,098 | B1 | 2/2011 | Simmons, Jr. |
| 7,883,531 | B2 | 2/2011 | De Coninck |
| 7,887,589 | B2 | 2/2011 | Glenn et al. |
| 7,887,591 | B2 | 2/2011 | Aebi et al. |
| 7,887,595 | B1 | 2/2011 | Pimenta |
| 7,909,870 | B2 | 3/2011 | Kraus |
| 7,909,877 | B2 | 3/2011 | Krueger et al. |
| 7,922,729 | B2 | 4/2011 | Michelson |
| 7,951,199 | B2 | 5/2011 | Miller |
| 7,985,231 | B2 | 7/2011 | Sankaran |
| 7,993,403 | B2 | 8/2011 | Foley et al. |
| 8,002,808 | B2 | 8/2011 | Morrison et al. |
| 8,007,523 | B2 | 8/2011 | Wagner et al. |
| 8,021,424 | B2 | 9/2011 | Beger et al. |
| 8,021,426 | B2 | 9/2011 | Segal et al. |
| 8,025,697 | B2 | 9/2011 | McClellan et al. |
| 8,034,109 | B2 | 10/2011 | Zwirkoski |
| 8,043,381 | B2 | 10/2011 | Hestad et al. |
| 8,062,375 | B2 | 11/2011 | Glerum et al. |
| 8,075,621 | B2 | 12/2011 | Michelson |
| 8,177,812 | B2 | 5/2012 | Sankaran |
| 8,187,329 | B2 | 5/2012 | Theofilos |
| 8,192,495 | B2 | 6/2012 | Simpson et al. |
| 8,206,423 | B2 | 6/2012 | Siegal |
| 8,216,312 | B2 | 7/2012 | Gray |
| 8,221,501 | B2 | 7/2012 | Eisermann et al. |
| 8,221,502 | B2 | 7/2012 | Branch, Jr. |
| 8,231,681 | B2 | 7/2012 | Castleman et al. |
| 8,236,029 | B2 | 8/2012 | Siegal |
| 8,236,058 | B2 | 8/2012 | Fabian et al. |
| 8,241,328 | B2 | 8/2012 | Siegal |
| 8,241,358 | B2 | 8/2012 | Butler et al. |
| 8,246,622 | B2 | 8/2012 | Siegal et al. |
| 8,257,442 | B2 | 9/2012 | Edie et al. |
| 8,267,939 | B2 | 9/2012 | Cipoletti et al. |
| 8,273,128 | B2 | 9/2012 | Oh et al. |
| 8,287,599 | B2 | 10/2012 | McGuckin, Jr. |
| 8,303,663 | B2 | 11/2012 | Jimenez et al. |
| 8,323,342 | B2 | 12/2012 | Schwab |
| 8,323,345 | B2 | 12/2012 | Sledge |
| 8,328,812 | B2 | 12/2012 | Siegal et al. |
| 8,328,852 | B2 | 12/2012 | Zehavi et al. |
| 8,337,559 | B2 | 12/2012 | Hansell et al. |
| 8,343,219 | B2 | 1/2013 | Allain et al. |
| 8,349,015 | B2 | 1/2013 | Bae et al. |
| 8,353,961 | B2 | 1/2013 | McClintock et al. |
| 8,357,200 | B2 | 1/2013 | Adl |
| 8,377,133 | B2 * | 2/2013 | Yuan ............. A61B 17/1671 623/17.14 |
| 8,382,842 | B2 | 2/2013 | Greenhalgh et al. |
| 8,398,713 | B2 | 3/2013 | Weiman |
| 8,403,990 | B2 | 3/2013 | Dryer et al. |
| 8,409,291 | B2 | 4/2013 | Blackwell et al. |
| 8,435,298 | B2 | 5/2013 | Weiman |
| 8,454,617 | B2 | 6/2013 | Schaller et al. |
| 8,454,694 | B2 | 6/2013 | Armstrong et al. |
| 8,460,385 | B1 * | 6/2013 | Wensel ............. A61B 17/864 623/17.16 |
| 8,460,387 | B2 | 6/2013 | Theofilos |
| 8,465,524 | B2 | 6/2013 | Siegal |
| 8,470,044 | B2 | 6/2013 | Bertholet et al. |
| 8,480,747 | B2 | 7/2013 | Melkent et al. |
| 8,486,109 | B2 | 7/2013 | Siegal |
| 8,486,148 | B2 | 7/2013 | Butler et al. |
| 8,491,658 | B1 | 7/2013 | Etminan |
| 8,491,659 | B2 | 7/2013 | Weiman |
| 8,496,691 | B2 | 7/2013 | Blain |
| 8,496,708 | B2 | 7/2013 | Blain |
| 8,500,783 | B2 | 8/2013 | Baynham |
| 8,506,635 | B2 | 8/2013 | Palmatier et al. |
| 8,518,087 | B2 | 8/2013 | Lopez et al. |
| 8,518,120 | B2 | 8/2013 | Glerum et al. |
| 8,540,769 | B2 | 9/2013 | Janowski et al. |
| 8,551,173 | B2 | 10/2013 | Lechmann et al. |
| 8,551,175 | B1 * | 10/2013 | Wensel ............. A61F 2/447 623/17.11 |
| 8,556,979 | B2 | 10/2013 | Glerum et al. |
| 8,562,651 | B2 | 10/2013 | Metcalf et al. |
| 8,568,481 | B2 | 10/2013 | Olmos et al. |
| 8,579,977 | B2 | 11/2013 | Fabian |
| 8,579,981 | B2 | 11/2013 | Lim et al. |
| 8,591,585 | B2 | 11/2013 | McLaughlin et al. |
| 8,597,330 | B2 | 12/2013 | Siegal |
| 8,603,170 | B2 | 12/2013 | Cipoletti et al. |
| 8,613,772 | B2 | 12/2013 | Bray et al. |
| 8,617,245 | B2 | 12/2013 | Brett |
| 8,623,091 | B2 | 1/2014 | Suedkamp et al. |
| 8,628,576 | B2 | 1/2014 | Triplett et al. |
| 8,628,578 | B2 | 1/2014 | Miller et al. |
| 8,632,595 | B2 | 1/2014 | Weiman |
| 8,641,765 | B2 | 2/2014 | Muhanna |
| 8,663,329 | B2 | 3/2014 | Ernst |
| 8,668,740 | B2 | 3/2014 | Rhoda et al. |
| 8,672,977 | B2 | 3/2014 | Siegal et al. |
| 8,679,183 | B2 | 3/2014 | Glerum et al. |
| 8,685,098 | B2 | 4/2014 | Glerum et al. |
| 8,690,928 | B1 | 4/2014 | Walkenhorst et al. |
| 8,690,948 | B2 | 4/2014 | Armstrong et al. |
| 8,696,751 | B2 | 4/2014 | Ashley et al. |
| 8,709,086 | B2 | 4/2014 | Glerum |
| 8,715,351 | B1 | 5/2014 | Pinto |
| 8,721,723 | B2 | 5/2014 | Hansell et al. |
| 8,747,443 | B2 | 6/2014 | Aferzon |
| 8,753,398 | B2 | 6/2014 | Gordon et al. |
| 8,758,439 | B2 | 6/2014 | Linares |
| 8,764,831 | B2 | 7/2014 | Lechmann et al. |
| 8,771,360 | B2 | 7/2014 | Jimenez et al. |
| 8,777,993 | B2 | 7/2014 | Siegal et al. |
| 8,778,025 | B2 | 7/2014 | Ragab et al. |
| 8,795,366 | B2 | 8/2014 | Varela |
| 8,821,555 | B2 | 9/2014 | Bae et al. |
| 8,828,085 | B1 | 9/2014 | Jensen |
| 8,845,638 | B2 | 9/2014 | Siegal et al. |
| 8,845,731 | B2 | 9/2014 | Weiman |
| 8,845,732 | B2 | 9/2014 | Weiman |
| 8,845,734 | B2 | 9/2014 | Weiman |
| 8,852,279 | B2 | 10/2014 | Weiman |
| 8,864,833 | B2 | 10/2014 | Glerum et al. |
| 8,888,853 | B2 | 11/2014 | Glerum et al. |
| 8,888,854 | B2 | 11/2014 | Glerum et al. |
| 8,900,235 | B2 | 12/2014 | Siegal |
| 8,900,307 | B2 | 12/2014 | Hawkins et al. |
| 8,906,098 | B2 | 12/2014 | Siegal |
| 8,926,704 | B2 | 1/2015 | Glerum et al. |
| 8,932,359 | B2 | 1/2015 | Brett |
| 8,936,641 | B2 | 1/2015 | Cain |
| 8,940,052 | B2 | 1/2015 | Lechmann et al. |
| 8,956,416 | B2 | 2/2015 | McCarthy |
| 8,986,387 | B1 | 3/2015 | To et al. |
| 9,005,291 | B2 | 4/2015 | Loebl et al. |
| 9,005,293 | B2 | 4/2015 | Moskowitz et al. |
| 9,005,295 | B2 | 4/2015 | Kueenzi et al. |
| 9,017,408 | B2 | 4/2015 | Siegal et al. |
| 9,017,413 | B2 | 4/2015 | Siegal et al. |
| 9,039,767 | B2 | 5/2015 | Raymond et al. |
| 9,039,771 | B2 | 5/2015 | Glerum et al. |
| 9,044,334 | B2 | 6/2015 | Siegal et al. |
| 9,060,876 | B1 | 6/2015 | To et al. |
| 9,078,767 | B1 | 7/2015 | McLean |
| 9,091,488 | B2 | 7/2015 | Postma et al. |
| 9,095,446 | B2 | 8/2015 | Landry et al. |
| 9,095,447 | B2 | 8/2015 | Barreiro et al. |

(56) References Cited

U.S. PATENT DOCUMENTS

| | | |
|---|---|---|
| 9,101,488 B2 | 8/2015 | Malandain |
| 9,101,489 B2 | 8/2015 | Protopsaltis et al. |
| 9,107,766 B1 | 8/2015 | McLean et al. |
| 9,138,330 B2 | 9/2015 | Hansell et al. |
| 9,192,419 B2 | 11/2015 | McDonough et al. |
| 9,248,028 B2 | 2/2016 | Gamache |
| 9,254,138 B2 | 2/2016 | Siegal et al. |
| 9,265,546 B2 | 2/2016 | Blain |
| 9,265,621 B2 | 2/2016 | Voellmicke |
| 9,271,836 B2 | 3/2016 | Pavento et al. |
| 9,278,009 B2 | 3/2016 | Bray et al. |
| 9,283,092 B2 | 3/2016 | Siegal et al. |
| 9,289,311 B1 | 3/2016 | Whipple |
| 9,364,272 B2 | 6/2016 | Binder et al. |
| 9,402,735 B2 | 8/2016 | McDonough et al. |
| 9,402,738 B2 | 8/2016 | Niemiec et al. |
| 9,408,712 B2 | 8/2016 | Siegal et al. |
| 9,566,165 B2 * | 2/2017 | Lee ................ A61F 2/4425 |
| 9,662,225 B2 | 5/2017 | Pavento et al. |
| 9,668,877 B2 | 6/2017 | Pavento et al. |
| 9,918,851 B2 * | 3/2018 | Willis ................ A61F 2/447 |
| 9,987,142 B2 * | 6/2018 | McConnell ........... A61F 2/4455 |
| 2001/0031968 A1 | 10/2001 | Dorchak et al. |
| 2001/0032020 A1 | 10/2001 | Besselink |
| 2002/0029044 A1 | 3/2002 | Monassevitch et al. |
| 2002/0029082 A1 | 3/2002 | Muhanna |
| 2002/0068976 A1 | 6/2002 | Jackson |
| 2002/0068977 A1 | 6/2002 | Jackson |
| 2002/0095155 A1 | 7/2002 | Michelson |
| 2002/0099376 A1 | 7/2002 | Michelson |
| 2002/0128716 A1 | 9/2002 | Cohen et al. |
| 2002/0138146 A1 | 9/2002 | Jackson |
| 2002/0143328 A1 | 10/2002 | Shluzas et al. |
| 2002/0151976 A1 | 10/2002 | Foley et al. |
| 2002/0156475 A1 | 10/2002 | Lerch et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0023305 A1 | 1/2003 | McKay |
| 2003/0028197 A1 | 2/2003 | Hanson et al. |
| 2003/0040799 A1 | 2/2003 | Boyd et al. |
| 2003/0045940 A1 | 3/2003 | Eberlein et al. |
| 2003/0050645 A1 | 3/2003 | Parker et al. |
| 2003/0065396 A1 | 4/2003 | Michelson |
| 2003/0078667 A1 | 4/2003 | Manasas et al. |
| 2003/0083748 A1 | 5/2003 | Lee et al. |
| 2003/0100949 A1 | 5/2003 | Michelson |
| 2003/0125739 A1 | 7/2003 | Bagga et al. |
| 2003/0130739 A1 | 7/2003 | Gerbec et al. |
| 2003/0135275 A1 | 7/2003 | Garcia et al. |
| 2003/0139812 A1 | 7/2003 | Garcia et al. |
| 2003/0139813 A1 | 7/2003 | Messerli et al. |
| 2003/0153975 A1 | 8/2003 | Byrd et al. |
| 2003/0158555 A1 | 8/2003 | Sanders et al. |
| 2003/0187440 A1 | 10/2003 | Richelsoph et al. |
| 2003/0187506 A1 | 10/2003 | Ross et al. |
| 2003/0195632 A1 | 10/2003 | Foley et al. |
| 2003/0208203 A1 | 11/2003 | Lim et al. |
| 2003/0225409 A1 | 12/2003 | Freid et al. |
| 2003/0233145 A1 | 12/2003 | Landry et al. |
| 2004/0024464 A1 | 2/2004 | Errico et al. |
| 2004/0030387 A1 | 2/2004 | Landry et al. |
| 2004/0034430 A1 | 2/2004 | Falahee |
| 2004/0064144 A1 | 4/2004 | Johnson et al. |
| 2004/0087947 A1 | 5/2004 | Lim et al. |
| 2004/0088055 A1 | 5/2004 | Hanson et al. |
| 2004/0092929 A1 | 5/2004 | Zindrick |
| 2004/0106996 A1 | 6/2004 | Liu et al. |
| 2004/0111089 A1 | 6/2004 | Stevens et al. |
| 2004/0117022 A1 * | 6/2004 | Marnay ................ A61F 2/4425 |
| | | 623/17.16 |
| 2004/0127902 A1 | 7/2004 | Suzuki et al. |
| 2004/0127990 A1 | 7/2004 | Bartish et al. |
| 2004/0127991 A1 | 7/2004 | Ferree |
| 2004/0138662 A1 | 7/2004 | Landry et al. |
| 2004/0153065 A1 | 8/2004 | Lim |
| 2004/0153072 A1 | 8/2004 | Bonutti |
| 2004/0153156 A1 | 8/2004 | Cohen et al. |
| 2004/0162618 A1 | 8/2004 | Mujwid et al. |
| 2004/0167625 A1 | 8/2004 | Beyar et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0193269 A1 | 9/2004 | Fraser et al. |
| 2004/0199253 A1 | 10/2004 | Link et al. |
| 2004/0199254 A1 | 10/2004 | Louis et al. |
| 2004/0210219 A1 | 10/2004 | Bray |
| 2004/0230309 A1 | 11/2004 | Dimauro et al. |
| 2004/0249377 A1 | 12/2004 | Kaes et al. |
| 2004/0254644 A1 * | 12/2004 | Taylor ................ A61F 2/4425 |
| | | 623/17.13 |
| 2004/0260286 A1 | 12/2004 | Ferree |
| 2005/0015147 A1 * | 1/2005 | Schwardt ................ A61F 2/28 |
| | | 623/17.11 |
| 2005/0021144 A1 | 1/2005 | Malberg et al. |
| 2005/0033433 A1 | 2/2005 | Michelson |
| 2005/0038513 A1 | 2/2005 | Michelson |
| 2005/0038515 A1 | 2/2005 | Kunzler |
| 2005/0043800 A1 | 2/2005 | Paul et al. |
| 2005/0065608 A1 | 3/2005 | Michelson |
| 2005/0071006 A1 | 3/2005 | Kirschman |
| 2005/0071008 A1 | 3/2005 | Kirschman |
| 2005/0085913 A1 | 4/2005 | Fraser et al. |
| 2005/0096657 A1 | 5/2005 | Autericque et al. |
| 2005/0101960 A1 | 5/2005 | Fiere et al. |
| 2005/0113916 A1 | 5/2005 | Branch, Jr. |
| 2005/0113917 A1 | 5/2005 | Chae et al. |
| 2005/0113920 A1 | 5/2005 | Foley et al. |
| 2005/0125062 A1 | 6/2005 | Biedermann et al. |
| 2005/0143749 A1 | 6/2005 | Zalenski et al. |
| 2005/0143827 A1 | 6/2005 | Globerman et al. |
| 2005/0149192 A1 | 7/2005 | Zucherman et al. |
| 2005/0149193 A1 | 7/2005 | Zucherman et al. |
| 2005/0154391 A1 | 7/2005 | Doherty et al. |
| 2005/0159813 A1 | 7/2005 | Molz, IV |
| 2005/0159819 A1 * | 7/2005 | McCormack ...... A61B 17/1757 |
| | | 623/17.16 |
| 2005/0165483 A1 * | 7/2005 | Ray, III ................ A61F 2/4455 |
| | | 623/17.11 |
| 2005/0177236 A1 | 8/2005 | Mathieu et al. |
| 2005/0177240 A1 | 8/2005 | Blain |
| 2005/0177245 A1 | 8/2005 | Leatherbury et al. |
| 2005/0182416 A1 | 8/2005 | Lim et al. |
| 2005/0209696 A1 | 9/2005 | Lin et al. |
| 2005/0222681 A1 | 10/2005 | Richley et al. |
| 2005/0251260 A1 | 11/2005 | Gerber et al. |
| 2005/0256576 A1 | 11/2005 | Moskowitz et al. |
| 2005/0261768 A1 | 11/2005 | Trieu |
| 2005/0261769 A1 | 11/2005 | Moskowitz et al. |
| 2005/0277938 A1 | 12/2005 | Parsons |
| 2005/0278026 A1 | 12/2005 | Gordon et al. |
| 2005/0278036 A1 | 12/2005 | Leonard et al. |
| 2006/0025860 A1 | 2/2006 | Li |
| 2006/0030851 A1 | 2/2006 | Bray et al. |
| 2006/0058801 A1 | 3/2006 | Schlienger et al. |
| 2006/0058876 A1 | 3/2006 | McKinley |
| 2006/0079961 A1 | 4/2006 | Michelson |
| 2006/0085071 A1 | 4/2006 | Lechmann et al. |
| 2006/0100706 A1 | 5/2006 | Shadduck et al. |
| 2006/0116768 A1 | 6/2006 | Krueger et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0129424 A1 | 6/2006 | Chan |
| 2006/0136062 A1 | 6/2006 | Dinello et al. |
| 2006/0142765 A9 | 6/2006 | Dixon et al. |
| 2006/0142858 A1 | 6/2006 | Colleran et al. |
| 2006/0142863 A1 | 6/2006 | Fraser et al. |
| 2006/0152863 A1 | 7/2006 | Freitag et al. |
| 2006/0178745 A1 | 8/2006 | Bartish et al. |
| 2006/0190083 A1 | 8/2006 | Arnin et al. |
| 2006/0206207 A1 | 9/2006 | Dryer et al. |
| 2006/0211952 A1 | 9/2006 | Kennedy, II |
| 2006/0229609 A1 | 10/2006 | Wang |

(56) References Cited

U.S. PATENT DOCUMENTS

| | | | |
|---|---|---|---|
| 2006/0229724 A1* | 10/2006 | Lechmann | A61F 2/4425 623/17.11 |
| 2006/0229725 A1 | 10/2006 | Lechmann et al. | |
| 2006/0229729 A1 | 10/2006 | Gordon et al. | |
| 2006/0235403 A1 | 10/2006 | Blain | |
| 2006/0235409 A1 | 10/2006 | Blain | |
| 2006/0235411 A1 | 10/2006 | Blain et al. | |
| 2006/0235518 A1 | 10/2006 | Blain | |
| 2006/0235531 A1 | 10/2006 | Buettner-Janz | |
| 2006/0235535 A1 | 10/2006 | Ferree et al. | |
| 2006/0241597 A1 | 10/2006 | Mitchell et al. | |
| 2006/0241761 A1 | 10/2006 | Gately | |
| 2006/0247650 A1 | 11/2006 | Yerby et al. | |
| 2006/0253201 A1 | 11/2006 | McLuen | |
| 2006/0259147 A1 | 11/2006 | Krishna et al. | |
| 2006/0265068 A1 | 11/2006 | Schwab | |
| 2006/0265075 A1 | 11/2006 | Baumgartner et al. | |
| 2006/0265077 A1 | 11/2006 | Zwirkoski | |
| 2006/0293753 A1 | 12/2006 | Thramann | |
| 2007/0010886 A1 | 1/2007 | Banick et al. | |
| 2007/0049941 A1 | 3/2007 | Thramann | |
| 2007/0055252 A1 | 3/2007 | Blain et al. | |
| 2007/0055377 A1 | 3/2007 | Hanson et al. | |
| 2007/0067035 A1 | 3/2007 | Falahee | |
| 2007/0073398 A1 | 3/2007 | Fabian et al. | |
| 2007/0106384 A1 | 5/2007 | Bray et al. | |
| 2007/0106388 A1 | 5/2007 | Michelson | |
| 2007/0118222 A1 | 5/2007 | Lang | |
| 2007/0129804 A1 | 6/2007 | Bentley et al. | |
| 2007/0149978 A1 | 6/2007 | Shezifi et al. | |
| 2007/0162138 A1 | 7/2007 | Heinz | |
| 2007/0173939 A1 | 7/2007 | Kim et al. | |
| 2007/0191959 A1 | 8/2007 | Hartmann et al. | |
| 2007/0198016 A1 | 8/2007 | Zang et al. | |
| 2007/0198089 A1 | 8/2007 | Moskowitz et al. | |
| 2007/0208423 A1 | 9/2007 | Messerli et al. | |
| 2007/0213737 A1 | 9/2007 | Schermerhorn et al. | |
| 2007/0213820 A1 | 9/2007 | Magerl et al. | |
| 2007/0219634 A1 | 9/2007 | Greenhalgh et al. | |
| 2007/0219635 A1 | 9/2007 | Mathieu et al. | |
| 2007/0233118 A1 | 10/2007 | McLain | |
| 2007/0233244 A1 | 10/2007 | Lopez et al. | |
| 2007/0233253 A1 | 10/2007 | Bray et al. | |
| 2007/0233261 A1 | 10/2007 | Lopez et al. | |
| 2007/0233263 A1 | 10/2007 | Melkent et al. | |
| 2007/0250167 A1 | 10/2007 | Bray et al. | |
| 2007/0255146 A1 | 11/2007 | Andrews et al. | |
| 2007/0255416 A1 | 11/2007 | Melkent et al. | |
| 2007/0265631 A1 | 11/2007 | Fox | |
| 2007/0270957 A1 | 11/2007 | Heinz | |
| 2007/0270965 A1 | 11/2007 | Ferguson | |
| 2007/0270968 A1 | 11/2007 | Baynham et al. | |
| 2007/0276375 A1 | 11/2007 | Rapp | |
| 2007/0276490 A1 | 11/2007 | Mateyka | |
| 2007/0282443 A1 | 12/2007 | Globerman et al. | |
| 2007/0282449 A1 | 12/2007 | De et al. | |
| 2007/0293948 A1 | 12/2007 | Bagga et al. | |
| 2007/0299521 A1 | 12/2007 | Glenn et al. | |
| 2008/0009877 A1 | 1/2008 | Sankaran et al. | |
| 2008/0015694 A1 | 1/2008 | Tribus | |
| 2008/0015701 A1 | 1/2008 | Garcia et al. | |
| 2008/0021556 A1 | 1/2008 | Edie | |
| 2008/0021558 A1 | 1/2008 | Thramann | |
| 2008/0027550 A1 | 1/2008 | Link et al. | |
| 2008/0033440 A1* | 2/2008 | Moskowitz | A61B 17/0642 606/251 |
| 2008/0051890 A1 | 2/2008 | Waugh et al. | |
| 2008/0051897 A1 | 2/2008 | Lopez et al. | |
| 2008/0058944 A1 | 3/2008 | Duplessis et al. | |
| 2008/0065219 A1 | 3/2008 | Dye | |
| 2008/0077247 A1 | 3/2008 | Murillo et al. | |
| 2008/0082173 A1 | 4/2008 | Delurio et al. | |
| 2008/0097436 A1 | 4/2008 | Culbert et al. | |
| 2008/0103597 A1 | 5/2008 | Lechmann et al. | |
| 2008/0103598 A1 | 5/2008 | Trudeau et al. | |
| 2008/0109005 A1 | 5/2008 | Trudeau et al. | |
| 2008/0119933 A1 | 5/2008 | Aebi et al. | |
| 2008/0125865 A1 | 5/2008 | Abdelgany | |
| 2008/0132949 A1 | 6/2008 | Aferzon et al. | |
| 2008/0132958 A1 | 6/2008 | Pech et al. | |
| 2008/0133012 A1 | 6/2008 | McGuckin | |
| 2008/0133014 A1 | 6/2008 | Gately et al. | |
| 2008/0140207 A1 | 6/2008 | Olmos et al. | |
| 2008/0147193 A1 | 6/2008 | Matthis et al. | |
| 2008/0161922 A1* | 7/2008 | Rhoda | A61F 2/44 623/17.11 |
| 2008/0161925 A1 | 7/2008 | Brittan et al. | |
| 2008/0167657 A1 | 7/2008 | Greenhalgh | |
| 2008/0167666 A1 | 7/2008 | Fiere et al. | |
| 2008/0172128 A1 | 7/2008 | Perez-Cruet et al. | |
| 2008/0177307 A1 | 7/2008 | Moskowitz et al. | |
| 2008/0177388 A1 | 7/2008 | Patterson et al. | |
| 2008/0183204 A1 | 7/2008 | Greenhalgh et al. | |
| 2008/0183293 A1 | 7/2008 | Parry et al. | |
| 2008/0183294 A1 | 7/2008 | Adl | |
| 2008/0195209 A1 | 8/2008 | Garcia et al. | |
| 2008/0221690 A1 | 9/2008 | Chaput et al. | |
| 2008/0221694 A1 | 9/2008 | Warnick et al. | |
| 2008/0234822 A1 | 9/2008 | Govil et al. | |
| 2008/0243136 A1 | 10/2008 | Prager et al. | |
| 2008/0243251 A1 | 10/2008 | Stad et al. | |
| 2008/0243254 A1 | 10/2008 | Butler | |
| 2008/0249569 A1 | 10/2008 | Waugh et al. | |
| 2008/0249575 A1 | 10/2008 | Waugh et al. | |
| 2008/0249622 A1 | 10/2008 | Gray | |
| 2008/0249625 A1 | 10/2008 | Waugh et al. | |
| 2008/0255620 A1 | 10/2008 | Strauss et al. | |
| 2008/0269806 A1 | 10/2008 | Zhang et al. | |
| 2008/0281425 A1 | 11/2008 | Thalgott et al. | |
| 2008/0294262 A1 | 11/2008 | Levieux | |
| 2008/0300601 A1 | 12/2008 | Fabian et al. | |
| 2008/0300634 A1 | 12/2008 | Gray | |
| 2008/0306596 A1 | 12/2008 | Jones et al. | |
| 2008/0306598 A1 | 12/2008 | Hansen et al. | |
| 2008/0312698 A1 | 12/2008 | Bergeron et al. | |
| 2008/0312742 A1 | 12/2008 | Abernathie | |
| 2008/0312743 A1 | 12/2008 | Vila et al. | |
| 2009/0005873 A1 | 1/2009 | Slivka et al. | |
| 2009/0012529 A1 | 1/2009 | Blain et al. | |
| 2009/0030421 A1 | 1/2009 | Hawkins et al. | |
| 2009/0030423 A1 | 1/2009 | Puno | |
| 2009/0030519 A1 | 1/2009 | Falahee | |
| 2009/0030520 A1* | 1/2009 | Biedermann | A61B 17/8033 623/17.16 |
| 2009/0054991 A1 | 2/2009 | Biyani et al. | |
| 2009/0062921 A1 | 3/2009 | Michelson | |
| 2009/0076610 A1 | 3/2009 | Afzal | |
| 2009/0088849 A1 | 4/2009 | Armstrong et al. | |
| 2009/0099554 A1 | 4/2009 | Forster et al. | |
| 2009/0099568 A1 | 4/2009 | Lowry et al. | |
| 2009/0099610 A1 | 4/2009 | Johnson et al. | |
| 2009/0099661 A1 | 4/2009 | Bhattacharya et al. | |
| 2009/0105771 A1 | 4/2009 | Lei et al. | |
| 2009/0105774 A1 | 4/2009 | Jones et al. | |
| 2009/0105830 A1 | 4/2009 | Jones et al. | |
| 2009/0105831 A1 | 4/2009 | Jones et al. | |
| 2009/0105832 A1 | 4/2009 | Allain et al. | |
| 2009/0112320 A1 | 4/2009 | Kraus | |
| 2009/0112324 A1 | 4/2009 | Refai et al. | |
| 2009/0125028 A1 | 5/2009 | Teisen et al. | |
| 2009/0131988 A1 | 5/2009 | Bush et al. | |
| 2009/0132054 A1 | 5/2009 | Zeegers | |
| 2009/0143859 A1 | 6/2009 | McClellan et al. | |
| 2009/0164020 A1 | 6/2009 | Janowski et al. | |
| 2009/0182428 A1 | 7/2009 | McClellan et al. | |
| 2009/0182430 A1 | 7/2009 | Tyber et al. | |
| 2009/0192549 A1 | 7/2009 | Sanders et al. | |
| 2009/0192613 A1 | 7/2009 | Wing et al. | |
| 2009/0192615 A1 | 7/2009 | Tyber et al. | |
| 2009/0192616 A1 | 7/2009 | Zielinski | |
| 2009/0198245 A1 | 8/2009 | Phan | |
| 2009/0198287 A1 | 8/2009 | Chiu | |
| 2009/0198339 A1 | 8/2009 | Kleiner et al. | |
| 2009/0210062 A1 | 8/2009 | Thalgott et al. | |

(56) References Cited

U.S. PATENT DOCUMENTS

| | | |
|---|---|---|
| 2009/0210064 A1 | 8/2009 | Lechmann et al. |
| 2009/0222096 A1 | 9/2009 | Trieu |
| 2009/0222099 A1 | 9/2009 | Liu et al. |
| 2009/0224023 A1 | 9/2009 | Moskowitz et al. |
| 2009/0234364 A1 | 9/2009 | Crook |
| 2009/0234398 A1 | 9/2009 | Chirico et al. |
| 2009/0240333 A1* | 9/2009 | Trudeau .............. A61F 2/44 623/17.13 |
| 2009/0240335 A1 | 9/2009 | Arcenio et al. |
| 2009/0248092 A1 | 10/2009 | Bellas et al. |
| 2009/0248159 A1 | 10/2009 | Aflatoon |
| 2009/0259316 A1 | 10/2009 | Ginn et al. |
| 2009/0265007 A1* | 10/2009 | Colleran .............. A61F 2/4465 623/17.16 |
| 2009/0270873 A1 | 10/2009 | Fabian |
| 2009/0287251 A1 | 11/2009 | Bae et al. |
| 2009/0292361 A1 | 11/2009 | Lopez |
| 2009/0306779 A1 | 12/2009 | Ahn |
| 2009/0326543 A1 | 12/2009 | Fabian, Jr. |
| 2009/0326580 A1 | 12/2009 | Anderson et al. |
| 2009/0326589 A1 | 12/2009 | Lemoine et al. |
| 2010/0004747 A1 | 1/2010 | Lin |
| 2010/0016901 A1 | 1/2010 | Robinson |
| 2010/0016905 A1 | 1/2010 | Greenhalgh et al. |
| 2010/0016973 A1 | 1/2010 | De et al. |
| 2010/0023128 A1 | 1/2010 | Malberg |
| 2010/0030334 A1 | 2/2010 | Molz, IV |
| 2010/0036496 A1 | 2/2010 | Yu et al. |
| 2010/0042159 A1 | 2/2010 | Butler |
| 2010/0057206 A1* | 3/2010 | Duffield .............. A61F 2/442 623/17.16 |
| 2010/0069969 A1 | 3/2010 | Ampuero et al. |
| 2010/0070037 A1 | 3/2010 | Parry et al. |
| 2010/0078372 A1 | 4/2010 | Kerfoot |
| 2010/0087925 A1 | 4/2010 | Kostuik et al. |
| 2010/0106249 A1 | 4/2010 | Tyber et al. |
| 2010/0137987 A1 | 6/2010 | Diao et al. |
| 2010/0145457 A1 | 6/2010 | Felt et al. |
| 2010/0145459 A1 | 6/2010 | McDonough et al. |
| 2010/0145460 A1 | 6/2010 | McDonough et al. |
| 2010/0150301 A1 | 6/2010 | Chan et al. |
| 2010/0179594 A1 | 7/2010 | Theofilos et al. |
| 2010/0179656 A1 | 7/2010 | Theofilos |
| 2010/0185287 A1 | 7/2010 | Allard et al. |
| 2010/0185289 A1* | 7/2010 | Kirwan .............. A61F 2/4455 623/17.11 |
| 2010/0185292 A1 | 7/2010 | Hochschuler et al. |
| 2010/0204739 A1 | 8/2010 | Bae et al. |
| 2010/0204795 A1 | 8/2010 | Greenhalgh |
| 2010/0204796 A1 | 8/2010 | Bae et al. |
| 2010/0217325 A1 | 8/2010 | Hochschuler et al. |
| 2010/0217393 A1 | 8/2010 | Theofilos |
| 2010/0234956 A1 | 9/2010 | Attia et al. |
| 2010/0249935 A1 | 9/2010 | Slivka et al. |
| 2010/0249937 A1 | 9/2010 | Blain et al. |
| 2010/0262240 A1 | 10/2010 | Chavatte et al. |
| 2010/0268338 A1 | 10/2010 | Melkent et al. |
| 2010/0286777 A1 | 11/2010 | Errico et al. |
| 2010/0286781 A1 | 11/2010 | Bullard |
| 2010/0286783 A1 | 11/2010 | Lechmann et al. |
| 2010/0292696 A1 | 11/2010 | Chantelot et al. |
| 2010/0292737 A1 | 11/2010 | Suh |
| 2010/0305704 A1 | 12/2010 | Messerli et al. |
| 2010/0312345 A1 | 12/2010 | Duffield et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0009908 A1 | 1/2011 | Ferguson |
| 2011/0009966 A1 | 1/2011 | Michelson |
| 2011/0015675 A1 | 1/2011 | Howard et al. |
| 2011/0015745 A1 | 1/2011 | Bucci |
| 2011/0015747 A1 | 1/2011 | McManus et al. |
| 2011/0029082 A1 | 2/2011 | Hall |
| 2011/0035011 A1 | 2/2011 | Cain |
| 2011/0082550 A1 | 4/2011 | Yeh |
| 2011/0082555 A1 | 4/2011 | Martz et al. |
| 2011/0093074 A1 | 4/2011 | Glerum et al. |
| 2011/0098747 A1 | 4/2011 | Donner et al. |
| 2011/0106159 A1 | 5/2011 | Nazeck |
| 2011/0118843 A1 | 5/2011 | Mathieu et al. |
| 2011/0130835 A1 | 6/2011 | Ashley et al. |
| 2011/0130838 A1 | 6/2011 | Morgenstern Lopez |
| 2011/0144703 A1 | 6/2011 | Krause et al. |
| 2011/0144753 A1 | 6/2011 | Marchek et al. |
| 2011/0166656 A1 | 7/2011 | Thalgott et al. |
| 2011/0172716 A1 | 7/2011 | Glerum |
| 2011/0184415 A1 | 7/2011 | Anderson et al. |
| 2011/0190892 A1 | 8/2011 | Kirschman |
| 2011/0202136 A1 | 8/2011 | Brittan et al. |
| 2011/0208311 A1 | 8/2011 | Janowski |
| 2011/0213421 A1 | 9/2011 | Binder et al. |
| 2011/0230971 A1 | 9/2011 | Donner et al. |
| 2011/0251689 A1 | 10/2011 | Seifert et al. |
| 2011/0270261 A1 | 11/2011 | Mast et al. |
| 2011/0282453 A1 | 11/2011 | Greenhalgh et al. |
| 2011/0295371 A1 | 12/2011 | Moskowitz et al. |
| 2011/0301711 A1 | 12/2011 | Palmatier et al. |
| 2011/0301712 A1 | 12/2011 | Palmatier et al. |
| 2011/0319896 A1 | 12/2011 | Papenfuss et al. |
| 2011/0319898 A1 | 12/2011 | O'Neil et al. |
| 2011/0319998 A1 | 12/2011 | O'Neil et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0041559 A1 | 2/2012 | Melkent et al. |
| 2012/0071977 A1 | 3/2012 | Oglaza et al. |
| 2012/0071980 A1 | 3/2012 | Purcell et al. |
| 2012/0078371 A1 | 3/2012 | Gamache et al. |
| 2012/0078372 A1 | 3/2012 | Gamache et al. |
| 2012/0078373 A1 | 3/2012 | Gamache et al. |
| 2012/0083889 A1 | 4/2012 | Purcell et al. |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0150301 A1 | 6/2012 | Gamache et al. |
| 2012/0150303 A1 | 6/2012 | Linares |
| 2012/0158143 A1 | 6/2012 | Shapiro |
| 2012/0185049 A1 | 7/2012 | Varela |
| 2012/0191190 A1 | 7/2012 | Trieu |
| 2012/0197401 A1 | 8/2012 | Duncan et al. |
| 2012/0197403 A1 | 8/2012 | Merves |
| 2012/0197405 A1 | 8/2012 | Cuevas et al. |
| 2012/0203230 A1 | 8/2012 | Adams |
| 2012/0209331 A1 | 8/2012 | Michelson |
| 2012/0226319 A1 | 9/2012 | Armstrong et al. |
| 2012/0226357 A1 | 9/2012 | Varela |
| 2012/0253406 A1 | 10/2012 | Bae et al. |
| 2012/0290097 A1 | 11/2012 | Cipoletti et al. |
| 2012/0310350 A1 | 12/2012 | Farris et al. |
| 2012/0310352 A1 | 12/2012 | Dimauro et al. |
| 2013/0030536 A1 | 1/2013 | Rhoda et al. |
| 2013/0041471 A1 | 2/2013 | Siegal et al. |
| 2013/0060337 A1 | 3/2013 | Petersheim et al. |
| 2013/0073044 A1 | 3/2013 | Gamache |
| 2013/0079883 A1 | 3/2013 | Butler et al. |
| 2013/0085572 A1 | 4/2013 | Glerum et al. |
| 2013/0085574 A1 | 4/2013 | Sledge |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0166027 A1 | 6/2013 | Bellas |

(56) References Cited

U.S. PATENT DOCUMENTS

| | | |
|---|---|---|
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0238095 A1 | 9/2013 | Pavento et al. |
| 2013/0268080 A1 | 10/2013 | Melkent et al. |
| 2013/0310939 A1 | 11/2013 | Fabian et al. |
| 2013/0325071 A1 | 12/2013 | Niemiec et al. |
| 2013/0345813 A1 | 12/2013 | Frank et al. |
| 2014/0025169 A1 | 1/2014 | Lechmann et al. |
| 2014/0039622 A1 | 2/2014 | Glerum et al. |
| 2014/0039623 A1 | 2/2014 | Iott et al. |
| 2014/0046333 A1 | 2/2014 | Johnson et al. |
| 2014/0058513 A1 | 2/2014 | Gahman et al. |
| 2014/0067069 A1 | 3/2014 | Lopez |
| 2014/0067073 A1 | 3/2014 | Hauck |
| 2014/0107786 A1 | 4/2014 | Geisler et al. |
| 2014/0114415 A1 | 4/2014 | Tyber |
| 2014/0114423 A1 | 4/2014 | Suedkamp et al. |
| 2014/0128977 A1 | 5/2014 | Glerum et al. |
| 2014/0135930 A1 | 5/2014 | Georges |
| 2014/0135934 A1 | 5/2014 | Hansell et al. |
| 2014/0142705 A1 | 5/2014 | Duffield et al. |
| 2014/0142706 A1 | 5/2014 | Hansell et al. |
| 2014/0156009 A1 | 6/2014 | Armstrong et al. |
| 2014/0163683 A1 | 6/2014 | Seifert et al. |
| 2014/0172103 A1 | 6/2014 | O'Neil et al. |
| 2014/0172106 A1 | 6/2014 | To et al. |
| 2014/0180421 A1 | 6/2014 | Glerum et al. |
| 2014/0228959 A1 | 8/2014 | Niemiec et al. |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0277474 A1 | 9/2014 | Robinson et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2014/0336771 A1* | 11/2014 | Zambiasi ............ A61F 2/4455 623/17.16 |
| 2014/0364917 A1 | 12/2014 | Sandstrom et al. |
| 2015/0012097 A1 | 1/2015 | Ibarra et al. |
| 2015/0045894 A1 | 2/2015 | Hawkins et al. |
| 2015/0094812 A1 | 4/2015 | Cain |
| 2015/0094813 A1 | 4/2015 | Lechmann et al. |
| 2015/0112438 A1 | 4/2015 | McLean |
| 2015/0182347 A1 | 7/2015 | Robinson |
| 2015/0250606 A1 | 9/2015 | McLean |
| 2015/0257892 A1 | 9/2015 | Lechmann et al. |
| 2015/0297356 A1 | 10/2015 | Gamache et al. |
| 2015/0313721 A1 | 11/2015 | Gamache et al. |
| 2015/0374511 A1 | 12/2015 | Pavento et al. |
| 2016/0045325 A1 | 2/2016 | Bellas et al. |
| 2016/0128846 A1 | 5/2016 | Voellmicke |
| 2016/0213487 A1 | 7/2016 | Wilson et al. |
| 2016/0296342 A1* | 10/2016 | Woods ............... A61F 2/4455 |
| 2016/0317317 A1 | 11/2016 | Marchek et al. |
| 2016/0324662 A1 | 11/2016 | McDonough et al. |
| 2017/0065427 A1* | 3/2017 | Songer ............... A61F 2/4455 |
| 2017/0304068 A1 | 10/2017 | Bellas et al. |
| 2017/0312090 A1 | 11/2017 | Sharabani et al. |

FOREIGN PATENT DOCUMENTS

| | | |
|---|---|---|
| DE | 4012622 C1 | 7/1991 |
| DE | 19710392 | 7/1999 |
| DE | 202008001079 U1 | 3/2008 |
| EP | 0302719 A1 | 2/1989 |
| EP | 0974319 A2 | 1/2000 |
| EP | 1103236 A2 | 5/2001 |
| EP | 1290985 A2 | 3/2003 |
| EP | 1391189 A1 | 2/2004 |
| EP | 1470803 A1 | 10/2004 |
| EP | 1532949 A1 | 5/2005 |
| EP | 1541096 A1 | 6/2005 |
| EP | 1609444 A1 | 12/2005 |
| EP | 1683490 A2 | 7/2006 |
| EP | 1683593 A2 | 7/2006 |
| EP | 1774926 A2 | 4/2007 |
| EP | 1459711 B1 | 7/2007 |
| EP | 1698305 B1 | 8/2007 |
| EP | 1847240 A1 | 10/2007 |
| EP | 1506753 B1 | 9/2009 |
| EP | 1843723 B1 | 3/2010 |
| EP | 2368529 A1 | 9/2011 |
| EP | 2237748 B1 | 9/2012 |
| EP | 2764851 A1 | 8/2014 |
| FR | 2874814 A1 | 3/2006 |
| FR | 2894130 A1 | 6/2007 |
| GB | 0457673 A | 12/1936 |
| GB | 2220729 A | 1/1990 |
| GB | 2457673 A | 8/2009 |
| JP | 2003-526457 A | 9/2003 |
| JP | 2006-516456 A | 7/2006 |
| JP | 2006-524114 A | 10/2006 |
| JP | 2007-516808 | 6/2007 |
| JP | 2011-509766 A | 3/2011 |
| JP | 2012-508044 | 4/2012 |
| WO | 94/23654 A1 | 10/1994 |
| WO | 95/31158 A1 | 11/1995 |
| WO | 97/00054 A1 | 1/1997 |
| WO | 97/20526 A1 | 6/1997 |
| WO | 97/37620 A1 | 10/1997 |
| WO | 98/04217 A1 | 2/1998 |
| WO | 98/34568 A1 | 8/1998 |
| WO | 99/27864 A2 | 6/1999 |
| WO | 99/38463 A2 | 8/1999 |
| WO | 99/52473 A1 | 10/1999 |
| WO | 99/63914 A1 | 12/1999 |
| WO | 00/12033 A1 | 3/2000 |
| WO | 00/74605 A1 | 12/2000 |
| WO | 01/01894 A1 | 1/2001 |
| WO | 01/01895 A1 | 1/2001 |
| WO | 01/08864 A1 | 2/2001 |
| WO | 01/68004 A2 | 9/2001 |
| WO | 02/13732 A2 | 2/2002 |
| WO | 02/80819 | 10/2002 |
| WO | 03/05938 A1 | 1/2003 |
| WO | 03/05939 | 1/2003 |
| WO | 2003/003951 A1 | 1/2003 |
| WO | 03/47473 A2 | 6/2003 |
| WO | 03/57088 A1 | 7/2003 |
| WO | 03/70128 A1 | 8/2003 |
| WO | 03/90650 A1 | 11/2003 |
| WO | 2004/069106 A1 | 8/2004 |
| WO | 04/93749 A1 | 11/2004 |
| WO | 2005/020861 A1 | 3/2005 |
| WO | 2005/069106 A1 | 7/2005 |
| WO | 2005/112834 A2 | 12/2005 |
| WO | 2006/047587 A2 | 5/2006 |
| WO | 2006/058281 A2 | 6/2006 |
| WO | 2006/065419 A2 | 6/2006 |
| WO | 2006/081843 A1 | 8/2006 |
| WO | 2006/084057 A1 | 8/2006 |
| WO | 2007/003785 A1 | 1/2007 |
| WO | 2007/009107 A2 | 1/2007 |
| WO | 2007/028098 A2 | 3/2007 |
| WO | 2007/048012 A2 | 4/2007 |
| WO | 2007/065993 A2 | 6/2007 |
| WO | 2007/070751 A1 | 6/2007 |
| WO | 2007/079021 A2 | 7/2007 |
| WO | 2007/098288 A2 | 8/2007 |
| WO | 2007/118856 A1 | 10/2007 |
| WO | 2008/044057 A1 | 4/2008 |
| WO | 2008/149223 A2 | 12/2008 |
| WO | 2009/025841 A1 | 2/2009 |
| WO | 2009/064644 A1 | 5/2009 |
| WO | 2009/064787 A2 | 5/2009 |
| WO | 2009/091775 A2 | 7/2009 |

(56) References Cited

FOREIGN PATENT DOCUMENTS

| WO | 2009/092102 | A1 | 7/2009 |
|----|-------------|-----|---------|
| WO | 2009/124269 | A1 | 10/2009 |
| WO | 2009/136009 | A1 | 11/2009 |
| WO | 2009/143496 | A1 | 11/2009 |
| WO | 2010/028045 | A1 | 3/2010 |
| WO | 2010/033786 | A2 | 3/2010 |
| WO | 2010/054208 | A1 | 5/2010 |
| WO | 2010/068725 | A2 | 6/2010 |
| WO | 2010/092893 | A1 | 8/2010 |
| WO | 2010/099239 | A2 | 9/2010 |
| WO | 2010/121028 | A2 | 10/2010 |
| WO | 2010/148112 | A1 | 12/2010 |
| WO | 2011/008864 | A1 | 1/2011 |
| WO | 2011/035126 | A1 | 3/2011 |
| WO | 2011/080535 | A1 | 7/2011 |
| WO | 2011/142761 | A1 | 11/2011 |
| WO | 2012/009152 | A1 | 1/2012 |
| WO | 2012/056119 | A1 | 5/2012 |
| WO | 2012/089317 | A1 | 7/2012 |
| WO | 2012/135764 | A1 | 10/2012 |
| WO | 2013/006669 | A2 | 1/2013 |
| WO | 2013/018062 | A1 | 2/2013 |
| WO | 2013/023096 | A1 | 2/2013 |
| WO | 2013/025876 | A1 | 2/2013 |
| WO | 2013/043850 | A2 | 3/2013 |
| WO | 2013/062903 | A1 | 5/2013 |
| WO | 2013/082184 | A1 | 6/2013 |
| WO | 2013/096192 | A1 | 6/2013 |
| WO | 2013/158294 | A1 | 10/2013 |
| WO | 2013/173767 | A1 | 11/2013 |
| WO | 2013/184946 | A1 | 12/2013 |
| WO | 2013/191979 | A1 | 12/2013 |
| WO | 2014/018098 | A1 | 1/2014 |
| WO | 2014/026007 | A1 | 2/2014 |
| WO | 2014/035962 | A1 | 3/2014 |
| WO | 2014/088521 | A2 | 6/2014 |
| WO | 2014/116891 | A1 | 7/2014 |
| WO | 2014/144696 | A1 | 9/2014 |

OTHER PUBLICATIONS

U.S. Provisional Application filed Jul. 26, 2012 by Lechmann et al., entitled "Expandable Implant", U.S. Appl. No. 61/675,975.
U.S. Non-Provisional Application filed Apr. 13, 2015 by Cain, entitled "Expandable Intervertebral Implant", U.S. Appl. No. 14/685,402.
U.S. Non-Provisional Application filed Mar. 6, 2015 by Marden, entitled "Expandable Intervertebral Implant", U.S. Appl. No. 14/640,220.
U.S. Application filed Jul. 2, 2015 by Thommen et al., U.S. Appl. No. 14/790,866.
Stand Alone Intervertebral Fusion Device, U.S. Appl. No. 13/237,233.
Shin, Posterior Lumbar Interbody Fusion via a Unilateral Approach, Yonsei Medical Journal, 2006, pp. 319-325, vol. 47(3).
Search Report dated Jan. 20, 2012 for EP07855287.
Schmiedberg, Isolation and characterization of metallic wear debris from a dynamic intervertebral disc prosthesis, J. Biomed. Mater. Res., vol. 28 Issue 11, 1277-1288, Nov. 1994.
Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.
Removable, Bone-Securing Cover Plate for Intervertebral Fusion Cage, U.S. Appl. No. 13/235,106.
Polikeit, The importance of the endplate for interbody cages in the lumbar spine, Eur Spine J, 2003, pp. 556-561, vol. 12.
Pederson, "Thermal Assembly of a Biomimetic Mineral/Collagen Composite", Biomaterials, 2003, vol. 2, pp. 4881-4890, Elsevier.
PCT Written Opinion of the International Searching Authority, International Application No. PCT/US2013/029026, dated May 23, 2013, 9 pages.
Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.
Novel Implant Inserter Having a Laterally-Extending Dovetail Engagement Feature, U.S. Appl. No. 13/364,280.
Novel Implant Inserter Having a Laterally-Extending Dovetail Engagement Feature, U.S. Appl. No. 13/237,200.
Krbec, [Replacement of the vertebral body with an expansion implant (Synex)], Acta Chir Orthop Traumatol Cech, 2002, pp. 158-162, vol. 69(3).
Kemnitzer and Kohn, in the Handbook of Biodegradable Polymers, edited by Domb, et al., Hardwood Academic Press, pp. 251-272, 1997.
Kandziora", Biomechanical Comparison of Cervical Spine Interbody Fusion Cages", Spine, vol. 26, No. 17, pp. 1850-1857, 2001, Lippincott Williams & Wilkins, Inc.
Journal of Biomaterials Research, vol. 22, pp. 993-1009, 1988 by Cohn and Younes.
International Search Report dated Nov. 15, 2013 issued in PCT/US2013/045360, 4 pgs.
International Search Report dated May 23, 2013 issued in PCT/US2013/029026.
International Search Report dated Apr. 11, 2013 issued in PCT/US2012/070082, 3 pgs.
International Preliminary Report on Patentability, International Application No. PCT/US2013/029026, dated Sep. 9, 2014, 10 pages.
International Preliminary Report on Patentability, dated Jun. 24, 2014 issued in PCT/US2012/070082, 7 pgs.
International Preliminary Report on Patentability dated Dec. 23, 2014, issued in PCT/US2013/045360, 10 pgs.
International Patent Application No. PCT/US2013/029014, International Search Report dated Jul. 1, 2013, 7 pages.
Interbody Device With Opening to Allow Packing Graft and Other Biologies, U.S. Appl. No. 13/673,061.
Hunt, Expanable cage placement via a posterolateral approach in lumbar spine reconstructions, Journal of Neurosurgery: Spine, 2006, pp. 271-274, vol. 5.
Humphries, "Anterior Fusion of the Lumbar Spine Using an Internal Fixative Device", Surgical Forum, vol. IX, p. 770-773, American College of Surgeons, 1959, Chicago, IL.
Heller in Handbook of Biodegradable Polymers, edited by Domb, et al, Hardwood Academic Press, pp. 99-118 (1997).
Gore, Technique of Cervical Interbody Fusion, Clinical Orthopaedics and Related Research, 1984, pp. 191-195, No. 188.
Gercek, "Subsidence of Stand-Alone Cervical Cages in Anterior Interbody Fusion: Warning", Eur Spine J., vol. 12, pp. 513-516, 2003, Springer-Verlag.
Fusion Cage With In-Line Single Piece Fixation, U.S. Appl. No. 13/237,174.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
European Search Report dated Oct. 1, 2015 issued in European Application 13757720, 6 pages.
European Examination Report dated Mar. 19, 2014 for EP07855287. 4.
Cohn, "Polymer Preprints", ACS Division of Polymer Chemistry, vol. 30(1), 1989, p. 498, (e.g. PEO/PLA).
Chiang, Biomechanical Comparison of Instrumented Posterior Lumbar Interbody Fusion with One or Two Cages by Finite Element Analysis, Spine, 2006, pp. E682-E689, vol. 31(19), Liooincott Williams & Wilkins, Inc.
Cain, "New Stand-Alone Anterior Lumbar Inerbody Fusion Device: Bioemechanical Comparison with Established Fixation Techniques", Spine, vol. 30, No. 23, pp. 2631-2636, 2005, Lippincott Williams & Wilkins, Inc.
Allcock in The Encyclopedia of Polymer Science, vol. 13, pp. 31-41, Wiley Intersciences, John Wiley & Sons, 1988.

* cited by examiner

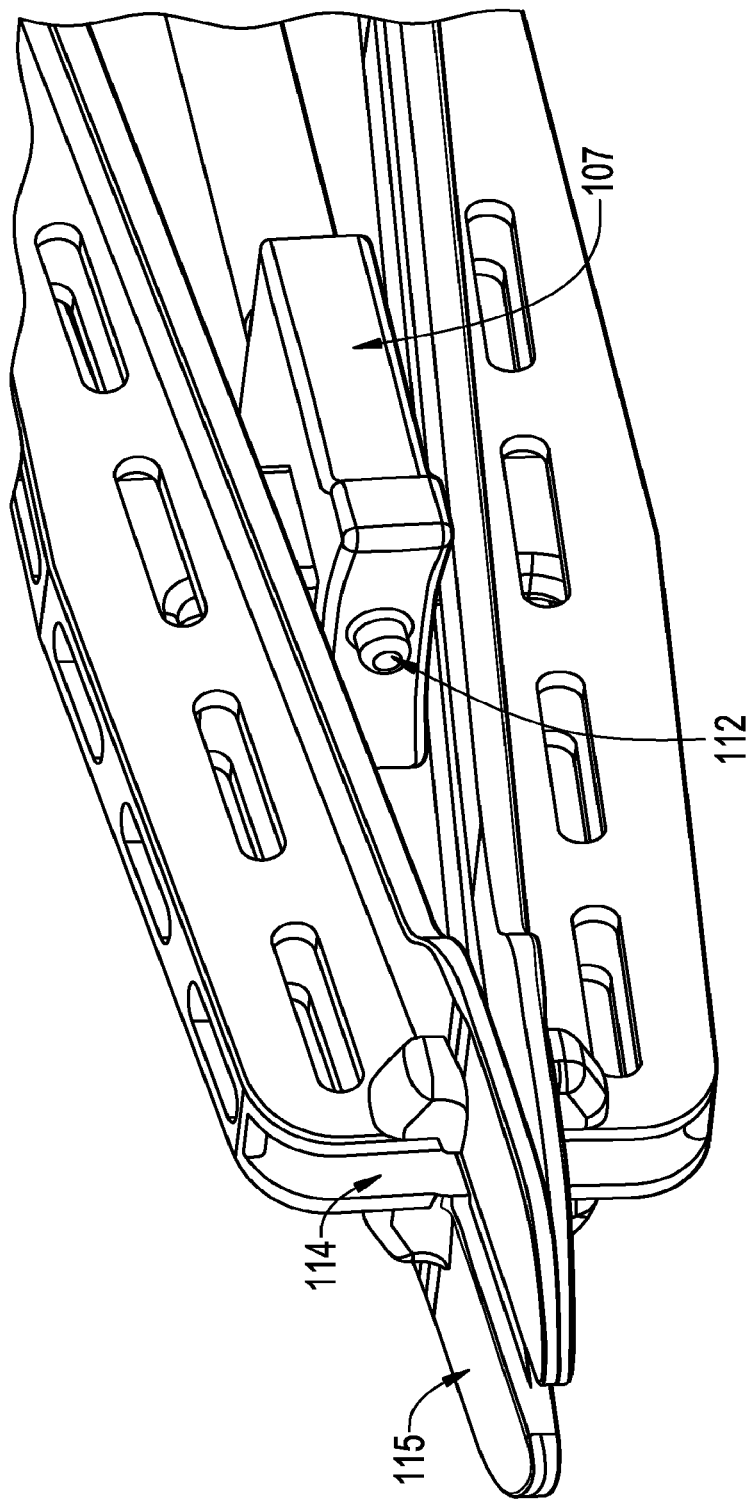

ZERO PROFILE SPINAL FUSION CAGE

CROSS-REFERENCE TO RELATED APPLICATIONS

This is a continuation application of U.S. patent application Ser. No. 12/414,532 filed Mar. 30, 2009, the disclosure of which is hereby incorporated by reference as if set forth in its entirety herein.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices" or "fusion cages".

Current interbody fusion techniques typically include not only an interbody fusion cage, but also supplemental fixation hardware such as fixation screws. This hardware adds to the time, cost, and complexity of the procedure. It also can result in tissue irritation when the cage's profile extends out of the disc space, thereby causing dysphonia/dysphagia in the cervical spine and vessel erosion in the lumbar spine. In addition, the fixation hardware typically includes a secondary locking feature, which adds to the bulkiness of the implant and time required for the procedure. Furthermore, existing fixation hardware may prevent the implantation of additional hardware at an adjacent location, and so require removal and potentially extensive revision of a previous procedure.

US Published Patent Application 2008-0312698 (Bergeron) discloses a device and system for stabilizing movement between two or more vertebral bodies and methods for implanting. Specifically, the embodiments provide medical professionals with the ability to selectively position and orient anchors in bony tissue and then attach a plate to the pre-positioned anchors. The plate assembly, once positioned on the anchors, prevents the anchors from backing out of the bony tissue. Furthermore, in situations in which it is desirable to provide spacing between two vertebral bodies, a spacer may be fixedly connected to the plates for positioning between two vertebral bodies. The spacer may further function as a lock out mechanism, or may be rotatably connected to the plates to maintain rotational freedom. The spacer may incorporate connection features or attachment features.

U.S. Pat. No. 4,904,261 (Dove) discloses a spinal implant, e.g., to replace an excised disc, comprising a rigid generally horseshoe shape of biocompatible material, such as carbon-fibre reinforced plastics, having upper and lower planar faces converging towards the ends of the horseshoe, and at least one hole from each planar face emerging in the outer curved face of the horseshoe, to enable the horseshoe to be fixed by screws inserted through one or more selected holes in each plurality from the ends in the outer curved face into respective adjacent vertebrae, with the screw heads bearing against shoulders, and with the space bounded by the inner curved face of the horseshoe available for the insertion of bone graft or a bone graft substitute.

U.S. Pat. No. 6,579,290 (Hardcastle) discloses a surgical implant for fusing adjacent vertebrae together comprising a body portion with spaced arms. The body portion has passages to receive surgical fixing screws engaged in holes drilled in the vertebrae for securing the body portion to the anterior faces of the vertebrae to be fused. The arms extend into a prepared space between the vertebrae to be fused. Graft material is packed between the arms. Each surgical fixing screw has an externally screw-threaded shank divided into wings which can be outwardly deformed to anchor the shank in the hole. Each surgical fixing screw also has a head which can be transformed between a laterally expanded condition and a laterally contracted condition to permit the head to be interlocked with the implant.

U.S. Pat. No. 6,342,074 (Simpson) discloses a spinal fusion implant and method for maintaining proper lumbar spine curvature and intervertebral disc spacing where a degenerative disc has been removed. The one-piece implant comprises a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopedic screw to be retained entirely within the access passage. A spinal fusion implant embodied in the present invention may be inserted anteriorly or laterally.

U.S. Pat. No. 6,972,019 (Michelson) discloses a spinal fusion implant for insertion between adjacent vertebral bodies that has opposed upper and lower surfaces adapted to contact each of the adjacent vertebral bodies from within the disc space, a leading end for insertion between the adjacent vertebral bodies, and a trailing end opposite the leading end. The trailing end has an exterior surface and an outer perimeter with an upper edge and a lower edge adapted to be oriented toward the adjacent vertebral bodies, respectively, and a plurality of bone screw receiving holes. At least one of the bone screw receiving holes is adapted to only partially circumferentially surround a trailing end of a bone screw received therein. At least one of the bone screw receiving holes passes through the exterior surface and one of the edges so as to permit the trailing end of the bone screw to protrude beyond one of the edges.

US Patent Publication 2009-0030520 (Biedermann) discloses a fixation device for bones that includes a member which is to be fixed to one or more bones and has at least one bore for receiving a bone screw, wherein the at least one bore comprises a first internal thread portion. The bone screw has a first shaft section provided with a first external thread portion arranged to cooperate with the internal thread portion of the at least one bore, and a head section having a diameter larger than that of the shaft section to provide a catch arranged to engage with a stop formed in the bore. The bone screw further has a second shaft section which includes a clearance groove extending between the catch of the head section and the external thread of the first shaft section. The clearance groove allows disengagement of the two thread portions, such that the bone screw is prevented from being unscrewed off the bore when it is loosened within the adjacent bone. The member can also include a side wall of a cage used in an intervertebral implant device, or can represent a plate of a bone plate assembly.

SUMMARY OF THE INVENTION

The present invention is directed to a method of fixing an intervertebral fusion cage in a disc space. In this method, a pair of fixation screws are first inserted into the opposing vertebral endplates within the disc space so that only their heads are exposed. These screw heads do not extend out of the disc space. Next, a novel cage (which has upper and lower longitudinal depressions that act as screw guide surfaces) is slid into the disc space using the screw heads as guides. When the cage is fully inserted, each screw head becomes seated in a distal (preferably, deeper) portion of the depression located in the proximal portion of the cage, thereby locking the cage in place. In this fixed condition, both the cage and the screw heads are located fully within the disc space and thereby provide a zero-profile assembly.

Therefore, in accordance with the present invention, there is provided an intervertebral fusion cage comprising:
 a) a proximal wall and a distal wall;
 b) first and second side walls connecting the proximal and distal walls, an upper bearing surface adapted for gripping an upper vertebral endplate and a lower bearing surface adapted for gripping a lower vertebral endplate, the upper bearing surface having at least one upper opening therethrough adapted to promote bony fusion, the lower bearing surface having at least one lower opening therethrough adapted to promote bony fusion, and
 c) a first guide surface canal formed in the upper bearing surface and extending substantially from the proximal wall to the distal wall, the canal adapted for distal reception of a first screw head.

Also in accordance with the present invention, there is provided an intervertebral fusion cage, comprising:
 a) a proximal wall and a distal wall,
 b) first and second side walls connecting the proximal and distal walls, an upper bearing surface adapted for gripping an upper vertebral endplate, and a lower bearing surface adapted for gripping a lower vertebral endplate, the upper bearing surface having at least one upper opening therethrough adapted to promote bony fusion, the lower bearing surface having at least one lower opening therethrough adapted to promote bony fusion,
 c) a first guide surface canal formed in the upper bearing surface and extending substantially from the proximal wall to the distal wall, and
 d) a first rail adapted for slidable reception in the first canal and having an outward opening recess adapted for reception of a first screw head.

Also in accordance with the present invention, there is provided a spinal assembly comprising:
 i) a first bone anchor comprising:
  a) a distal shaft, and
  b) a proximal screw head, and
 ii) an intervertebral fusion cage comprising:
  a) a proximal wall and a distal wall,
  b) first and second side walls connecting the proximal and distal walls, an upper bearing surface adapted for gripping an upper vertebral endplate and a lower bearing surface adapted for gripping a lower vertebral endplate, the upper bearing surface having at least one upper opening therethrough adapted to promote bony fusion, the lower bearing surface having at least one lower opening therethrough adapted to promote bony fusion,
  c) a first guide surface canal formed in the upper bearing surface and extending substantially from the proximal wall to the distal wall, the canal adapted for distal reception of the proximal screw head,
 wherein the first screw head is received in the canal.

DESCRIPTION OF THE FIGURES

FIGS. 18*a*-18*d* disclose various views of the inserter of the present invention.

Figure 1:
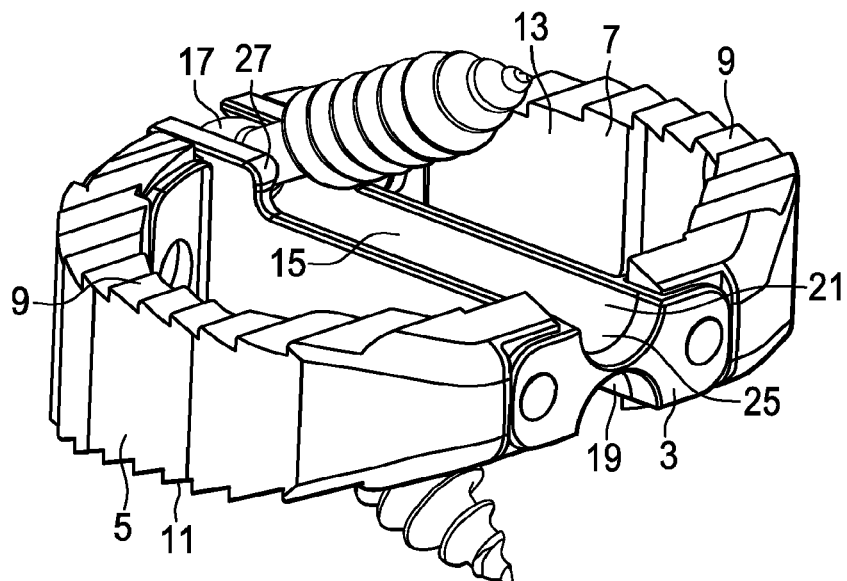
FIG. 1 discloses a first perspective view of a device of the present invention having a single screw and a single guide surface depression on each of the upper and lower bearing surfaces.
Figure 2:
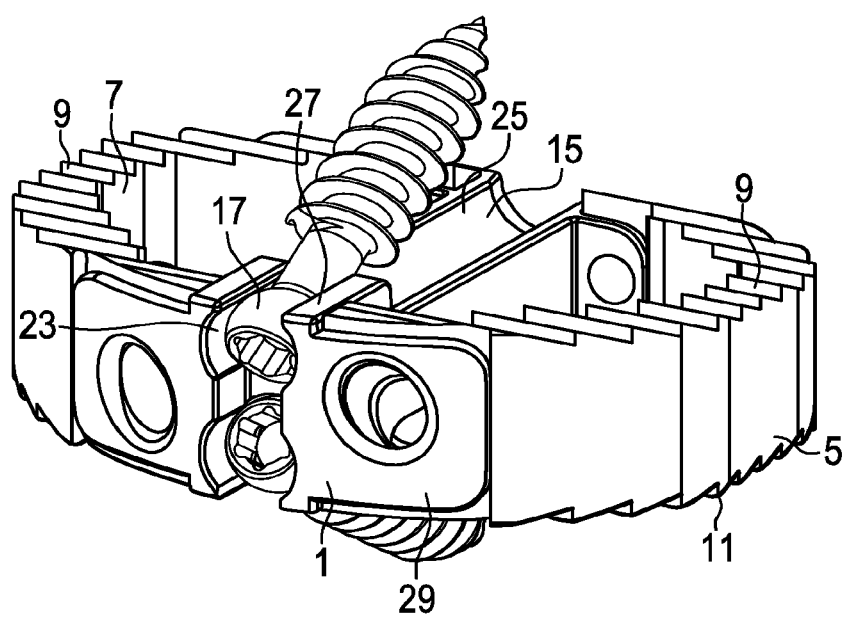
FIG. 2 discloses a second perspective view of the device of FIG. 1.

Now referring to FIGS. 1 and 2, there is provided an intervertebral fusion cage comprising:
  a) a proximal wall 1 and a distal wall 3,
  b) first 5 and second 7 side walls connecting the proximal and distal walls, an upper bearing surface 9 adapted for gripping an upper vertebral endplate and a lower bearing surface 11 adapted for gripping a lower vertebral endplate, the upper bearing surface having at least one upper opening 13 therethrough adapted to promote bony fusion, the lower bearing surface having at least one lower opening (not shown) therethrough adapted to promote bony fusion,
  c) a first guide surface depression 15 formed in the upper bearing surface and extending substantially from the proximal wall to the distal wall, the depression adapted for distal reception of a first sliding component comprising first screw head 17 and a threaded shank, and
  d) a second guide surface depression 19 formed in the lower bearing surface and extending substantially from the proximal wall to the distal wall, the second depression adapted for distal reception of a second sliding component comprising a second screw head and a threaded shank.

Typically, the guide surface depression forms a longitudinal canal in each bearing surface. The distal portion 21 of the guide surface depression acts as a means for guiding the more proximal portion of the canal to the screw head. When the proximal portion 23 of the canal is slid over the screw head, it envelops the screw head, thereby locking the cage in place. Further tightening of the screw can be performed to further lock the cage in place.

In some embodiments, the cross-sectional profile of the depression or canal is substantially equivalent to the cross-sectional profile of the screw head, so that the first depression is well adapted for distal-to-proximal translation of the first canal towards the screw head. In some preferred embodiments thereof, the screw head is substantially spherical, while the transverse cross-section of the first canal substantially forms a portion of a circle, thereby providing a substantially matching fit of the canal and screw head.

In some embodiments, the first canal extends substantially along a centerline of the cage, thereby allowing the use of a single screw per bearing surface.

In some preferred embodiments, the first canal comprises a distal recess 25 and a proximal process 27. The proximal process effectively acts to lock the cage in place when it slides over and envelops the screw head.

In some embodiments, the first canal includes an outwardly extending (longitudinal) bump (not shown) adapted to limit translational movement of the interbody device with respect to the screw. This bump acts as an additional means for guiding the deeper portion of the canal to the screw head, at which the cage becomes locked.

Figure 3:
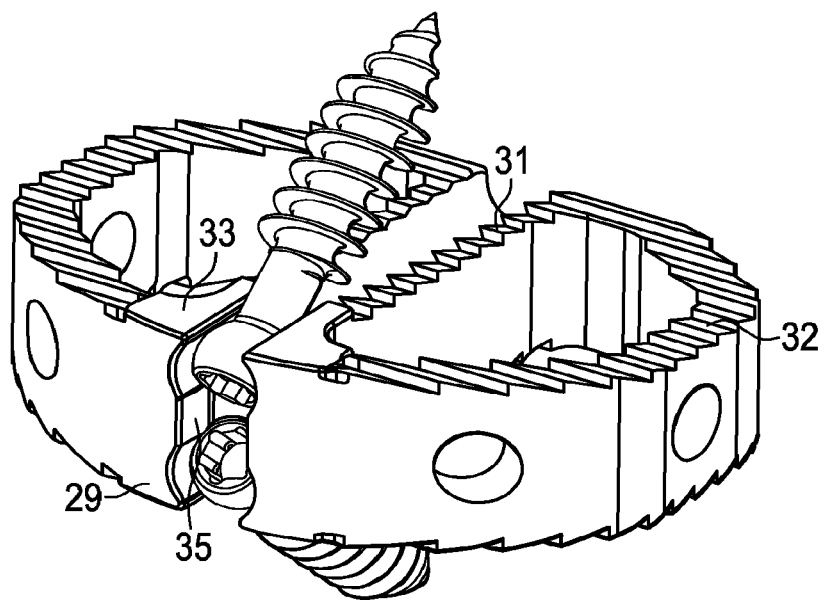
FIG. 3 discloses a device substantially similar to FIG. 1, but with teeth lining bearing surfaces bordering the guide surface depression.

Now referring to FIGS. 2 and 3, in some embodiments, additional strength is provided to the proximal portion 29 of the cage in order to withstand higher tensile forces and insertion forces. Preferably, this additional strength is achieved by using a stronger material in the proximal portion of the cage. In preferred embodiments thereof, the bearing surface 33 surrounding the proximal portion of the canal is formed from a metallic material.

In some embodiments, it is helpful to provide a final seating of the screw head once it becomes seated in the deeper proximal portion of the canal. In these embodiments, the proximal wall of the cage preferably has a vertical slot 35 that communicates with the horizontal guide surface canal and is adapted to allow access by a screwdriver. Thus, the surgeon has direct access to the screw head via a proximal route and can easily accomplish its final tightening.

Figure 4:
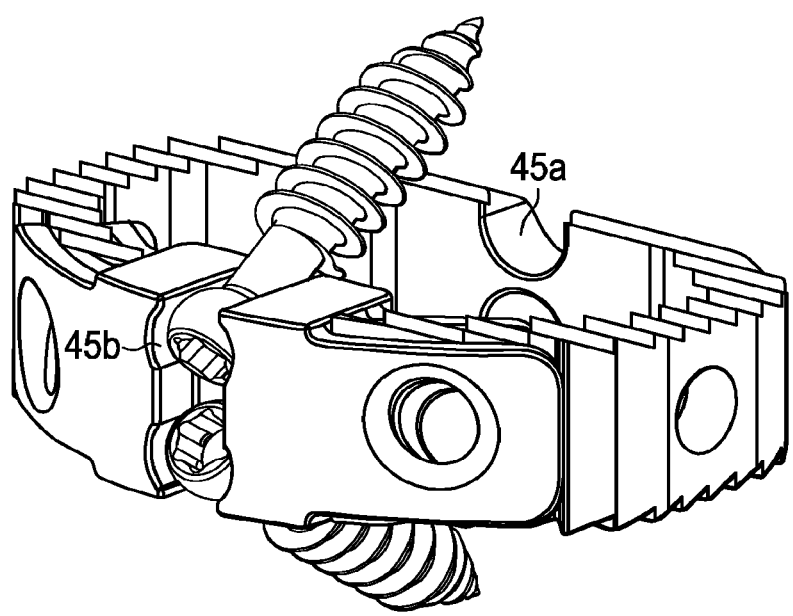
FIG. 4 discloses a device substantially similar to FIG. 1, but with a discontinuous guide surface depression.

In some embodiments (as in FIGS. 1-3), the guide surface canals are continuous longitudinal structures that guide the entry of the cage from the moment the canal contacts the screw head to the moment the screw seats in the proximal portion of the canal. However, in other embodiments (as in FIG. 4), the canal 45*a* and 45*b* may be discontinuous.

Figure 5:
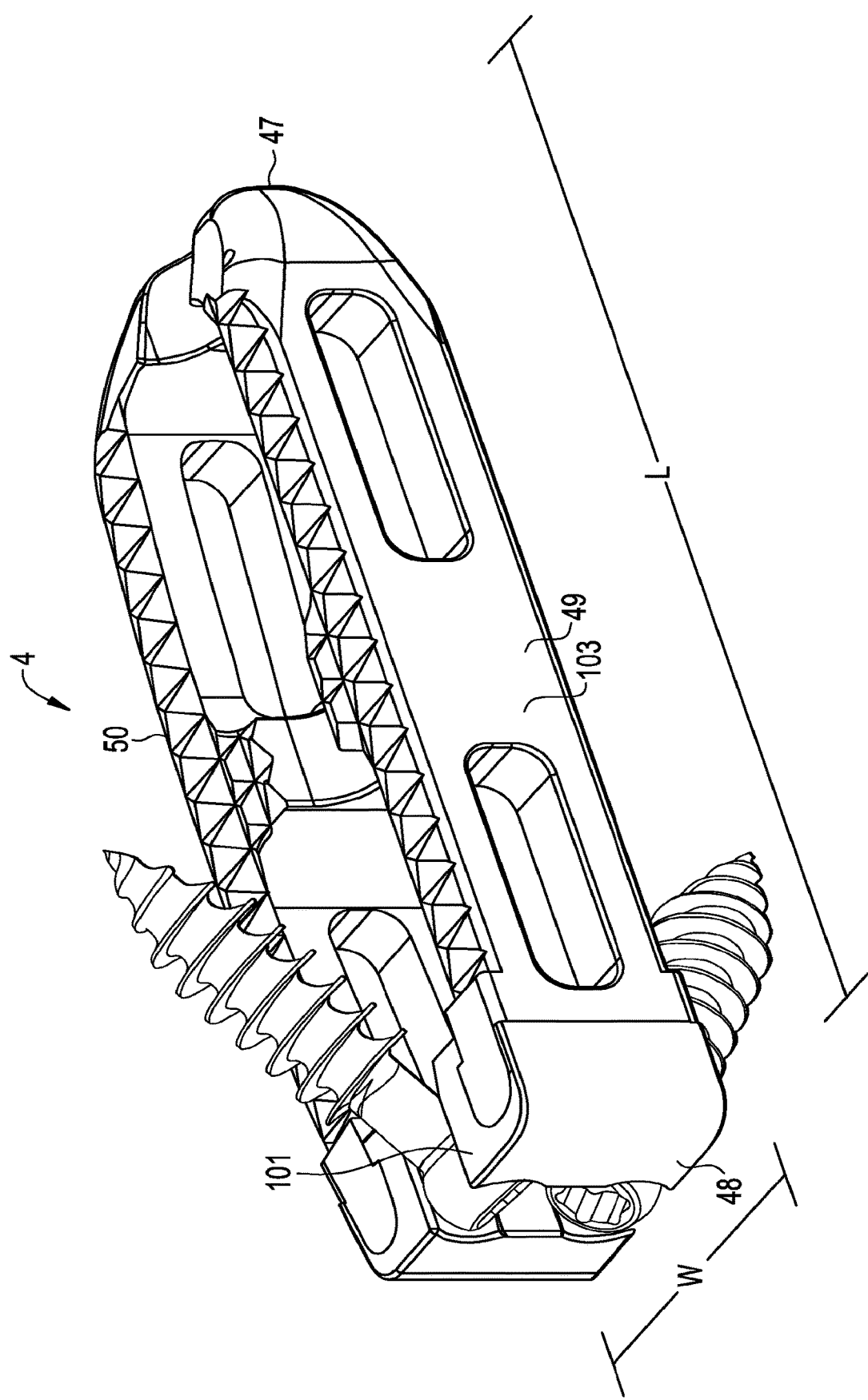
FIG. 5 discloses a device substantially similar to FIG. 4, but in a lateral cage configuration.

It is believed that the device of the present invention can be advantageously used in implanting lateral cages. Therefore, now referring to FIG. 5, there is provided a lateral cage 49 of the present invention, wherein the length L of the lateral cage (distal end 47 to proximal end 48 distance) is at least two times greater than the width W of the lateral cage (side wall 49 to side wall 50 length). Preferably, the length of the lateral cage is at least three times greater than the width of the lateral cage. Also in FIG. 5, the proximal portion 101 of the lateral cage is preferably made of a metal material such as titanium, while the distal portion 103 is made of a polymer-based material, such as CFRP.

Figure 6:
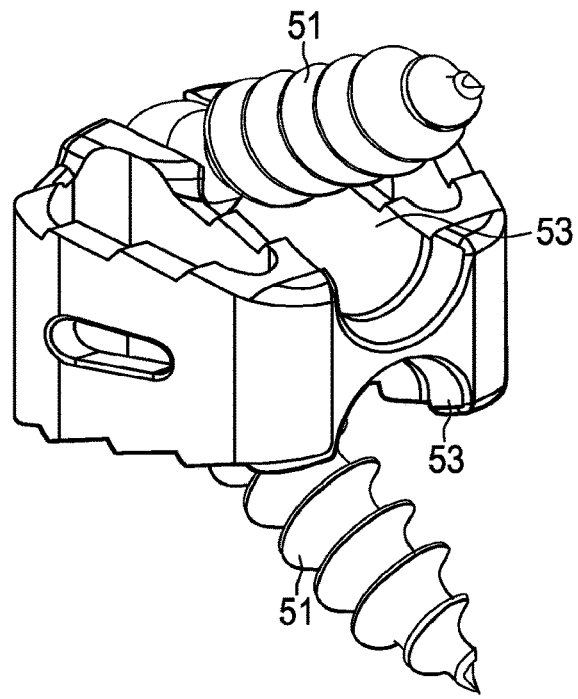
FIG. 6 discloses a first device substantially similar to FIG. 1, but with a cervical cage configuration.
Figure 7:
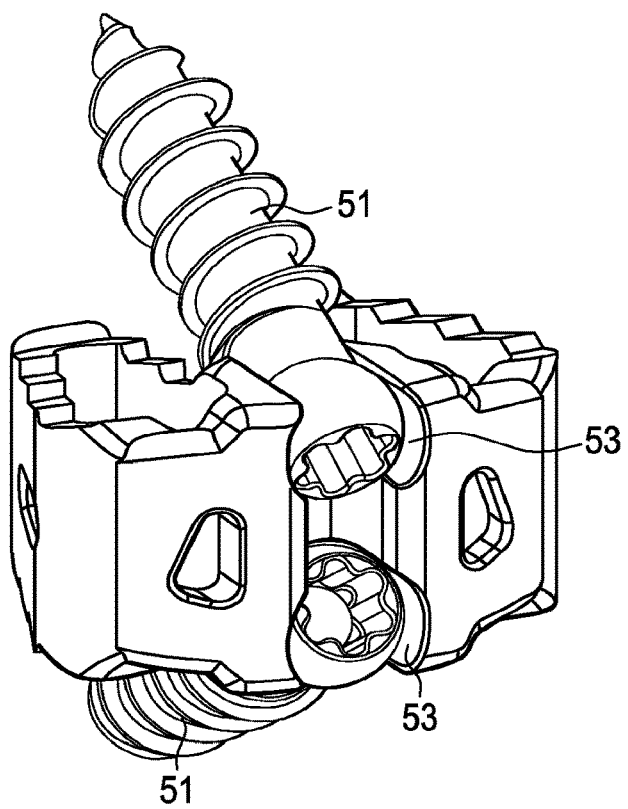
FIG. 7 discloses a second device substantially similar to FIG. 1, but with a cervical cage configuration.

It is believed that the device of the present invention can be advantageously used in implanting cervical cages. Therefore, now referring to FIGS. 6 and 7, there is provided a cervical cage of the present invention having a screw 51 extending from each guide surface depression 53.

In some embodiments, it is advantageous to add additional screws to the device in order to more completely secure the device to the vertebral endplates. Now referring to FIGS. 8 and 9, there is provided a first perspective view of a device having a pair of screws 55 inserted into the proximal wall 57 of the device and extending through the openings in the respective upper 59 and lower 61 bearing surfaces.

Figure 8:
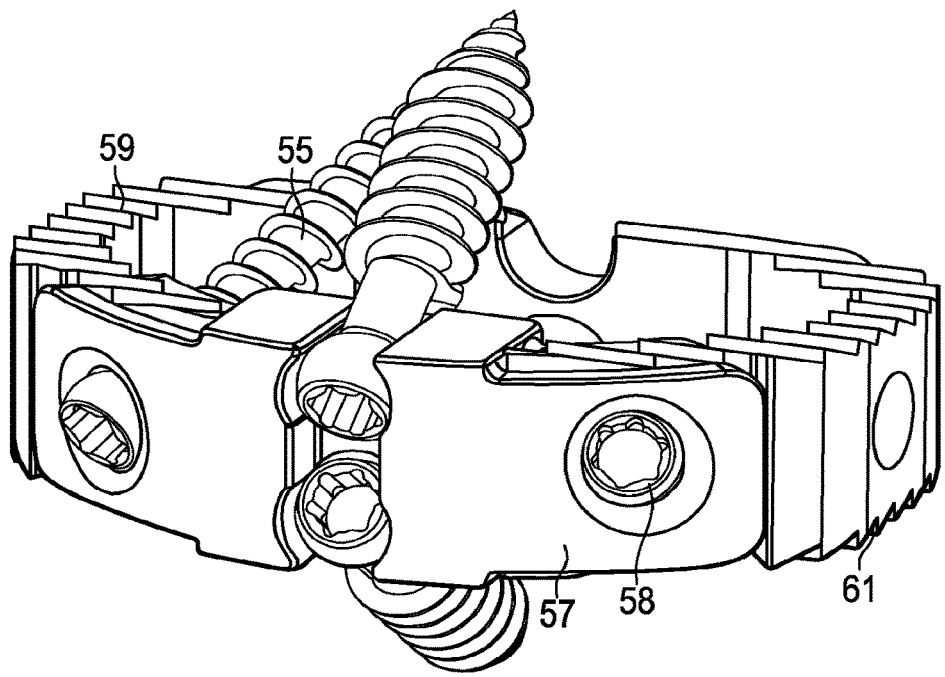
FIG. 8 discloses a first perspective view of a device substantially similar to FIG. 1, but with a pair of screws inserted into the proximal wall of the device and extending through the respective upper and lower bearing surfaces.
Figure 9:
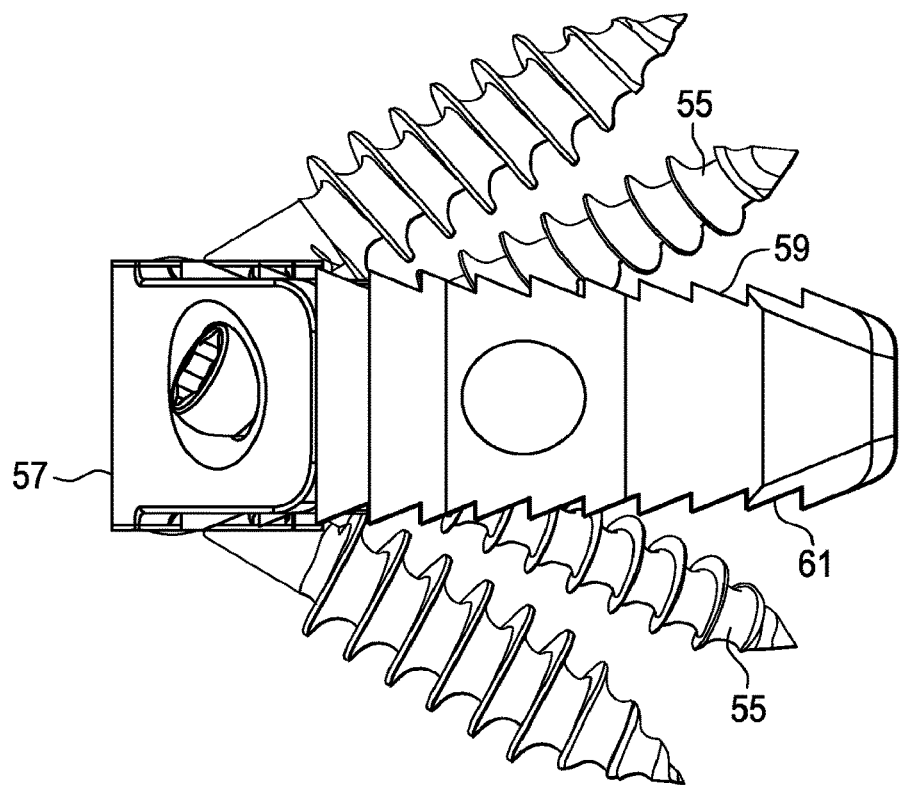
FIG. 9 discloses a side view of the cage of FIG. 8.
Figure 10:
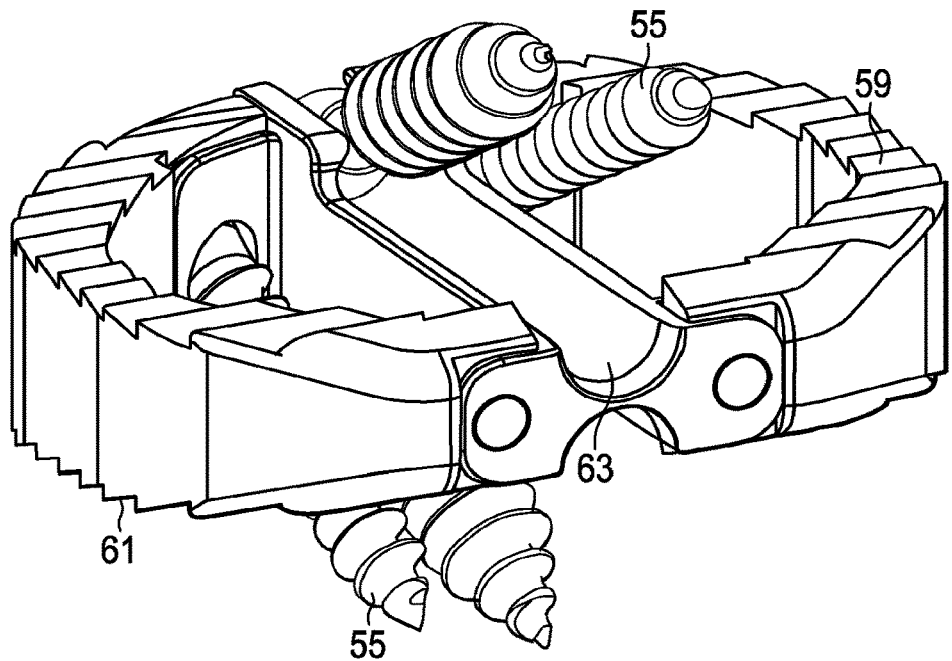
FIG. 10 discloses a first perspective view of a device substantially similar to the cage of FIG. 8, but with a continuous guide surface depression.
Figure 11:
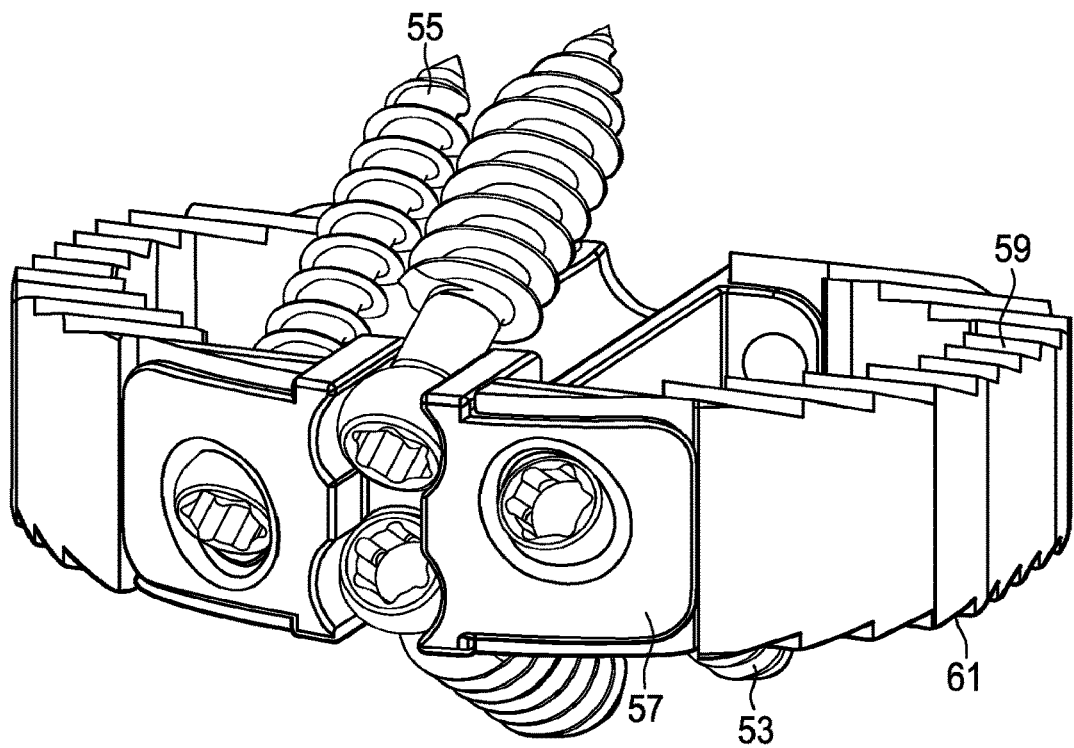
FIG. 11 discloses a first perspective view of the device of FIG. 10.

FIG. 10 discloses a distal perspective view of a device substantially similar to the cage of FIG. 8, but with a continuous guide surface depression 63. FIG. 11 discloses a proximal perspective view of the device of FIG. 10.

Various aspects of the present invention include an implant/instrument system, and a method of implantation. The present invention also includes a kit comprising:
  a) trial instruments comprising interbody spacing blocks having various sizes (height, angle, footprint), each with bone anchor placement guides.
  b) at least two bone fixation anchors to be placed into adjacent vertebral bodies while trialing with the aforementioned instrument, and c) an interbody implant configured for engaging with the heads of the implanted bone anchors after removing the trial instrument.

Figure 17A:
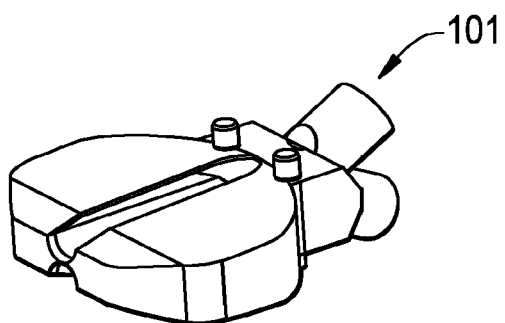
FIGS. 17*a* and 17*b* disclose a trial of the present invention.
Figure 17B:
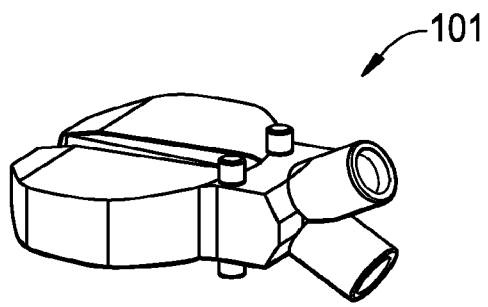
Figure 18A:
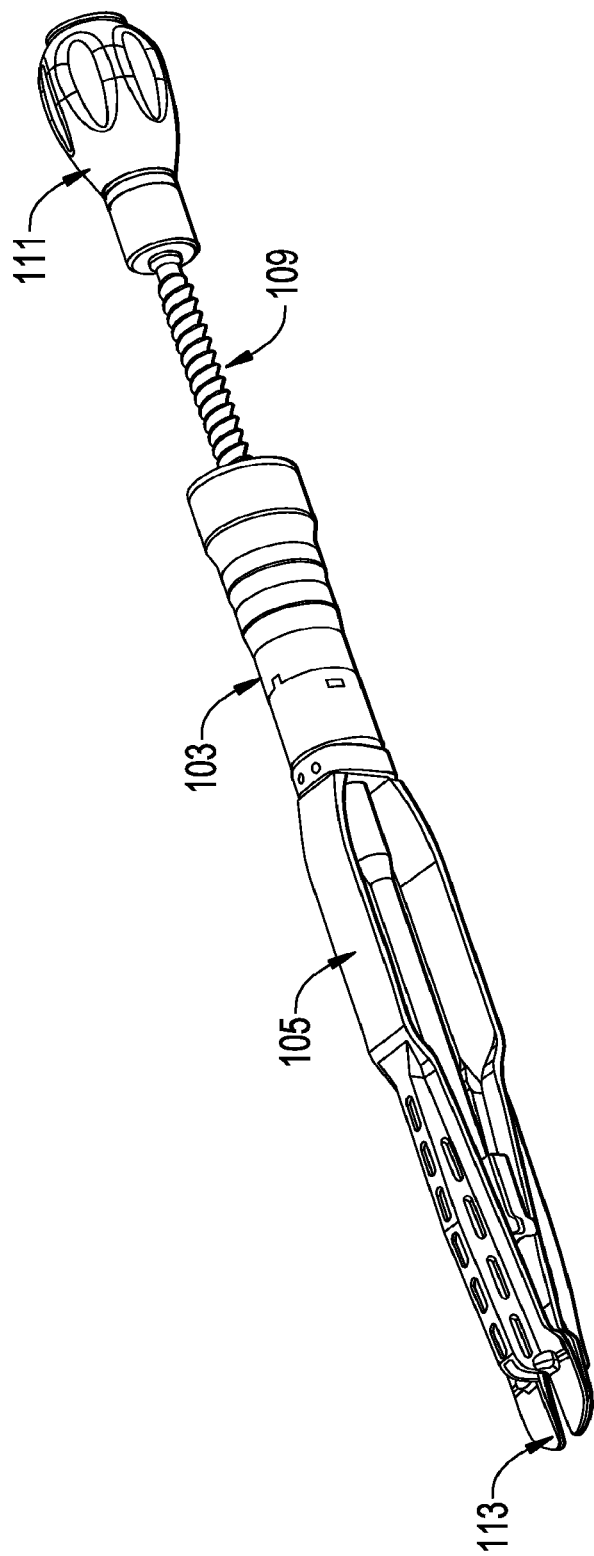
Figure 18C:
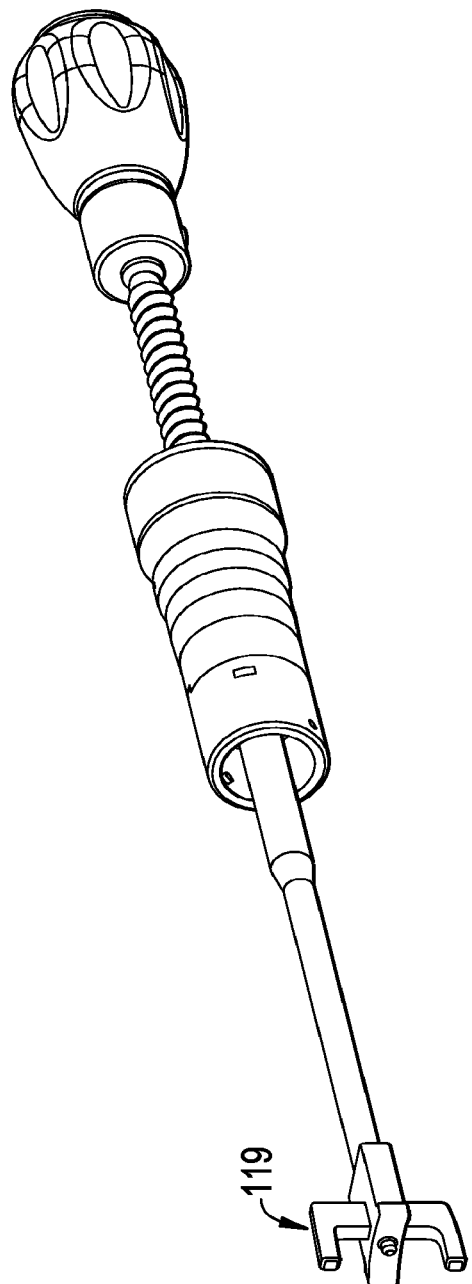
Figure 18D:
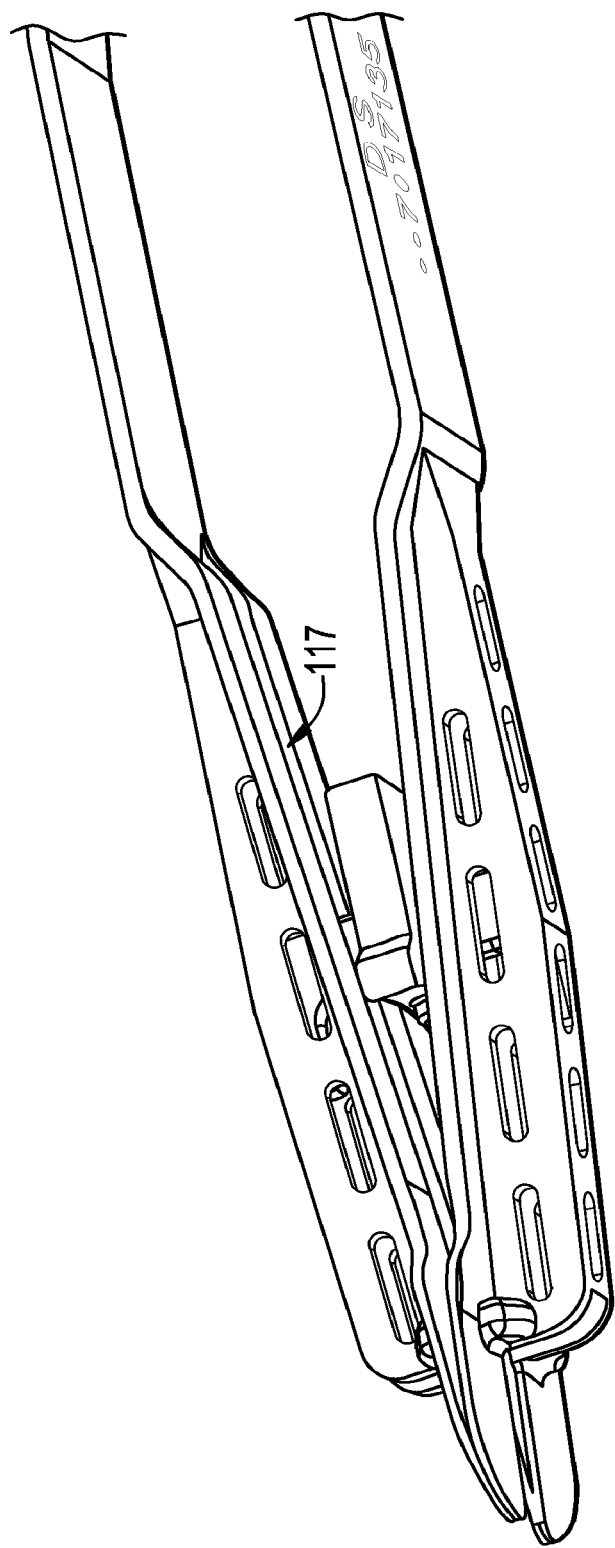

Now referring to FIGS. 17a and 17b, trial 101 has a handle attached to one side (not shown). Two pins are for the trial proper depth position. The vertebral body holes for anchoring the screws can be drilled through the guides.

The kit of the present invention allows the surgeon to fix the opposing vertebral bodies to one another through the interbody device without having the implant protrude outside of the disc space. Preferably, the heads of the bone anchors snap into proximal processes formed in canals located in the upper and lower surfaces of the interbody implant, thereby helping the implant resist migration. Preferably, the anchors can be inserted at various angles to accommodate anatomical differences as well as avoid any pre-existing hardware.

Preferably, the canals of the interbody implant sufficiently envelop the respective bone anchor heads so as to prevent back-out and pull-out of the anchor. In such situations, a secondary locking step/feature is not required. Preferably, the interbody implant allows passage therethrough of a driver to further seat and tighten the bone anchor into the bone after the implant has been placed. This is typically accomplished by a vertical slot 35 in the proximal wall that communicates with the canals. Preferably, the major diameter of the bone anchor is larger than the screw head diameter. In some embodiments, the major diameter is 5.5 mm). Larger major screw diameters can be used, as compared to conventional devices wherein the anchors are placed through the wall of the fixation device and limited by the height of the device. This is a major advantage.

The embodiments described herein are preferably designed for the cervical region, but also could be utilized for lumbar spine interbody fusion as well.

In a preferred embodiment of the invention shown in FIGS. 1 and 2, the bone anchor comprises a screw having a proximal head 17 that is substantially spherical such that it can accommodate variable angles and still engage with the interbody implant. Alternatively, other screw head shapes that match the shape of the canal recess and provide a reliable connection between two components may be used. Also, in preferred embodiments, the screws are positioned in the centerline so that they are less likely to interfere with an adjacent level plate with two screws in each vertebra, as some plates have screws positioned laterally so the screws of the present invention can go in between them. In use, the screws are first installed and then the interbody implant is slid between the vertebrae, using the insertion tool that aligns the central canals of the cage with the screw heads. In preferred embodiments, a small radial bump (not shown) located in the canal limits translational movement of the interbody device with respect to the screw. In another preferred embodiment, the screws are positioned such that upon sliding the interbody device into the disc space, the interbody device slides primarily over the screw heads (instead of primarily contacting the endplates—the screws are inserted slightly proud to allow larger distraction) to ease insertion. At the end of insertion, the screw heads "drop" into a larger proximal process of the canals, thereby ensuring that the upper and lower surfaces of the interbody device abut the bony endplates and providing the means of preventing the interbody device from backing out. The interbody device preferably has internal spaces opening outward through the upper and lower bearing surfaces and onto the adjacent bony endplates. These spaces may be packed with bone graft or bone graft substitute prior to implantation in order to promote bony fusion of the opposing endplates.

In some embodiments, the proximal wall of the cage has a small vertical slot 35 that provides access by a screwdriver shaft to the guide surface canals (and thereby the screw heads). After interbody device insertion into the disc space, the screws are preferably tightened through these slots to ensure construct stability. Screw backout is prevented by design of the cage and method of cage installation, as the screw heads are seated on the inner surfaces of the respective canals.

Figure 12:
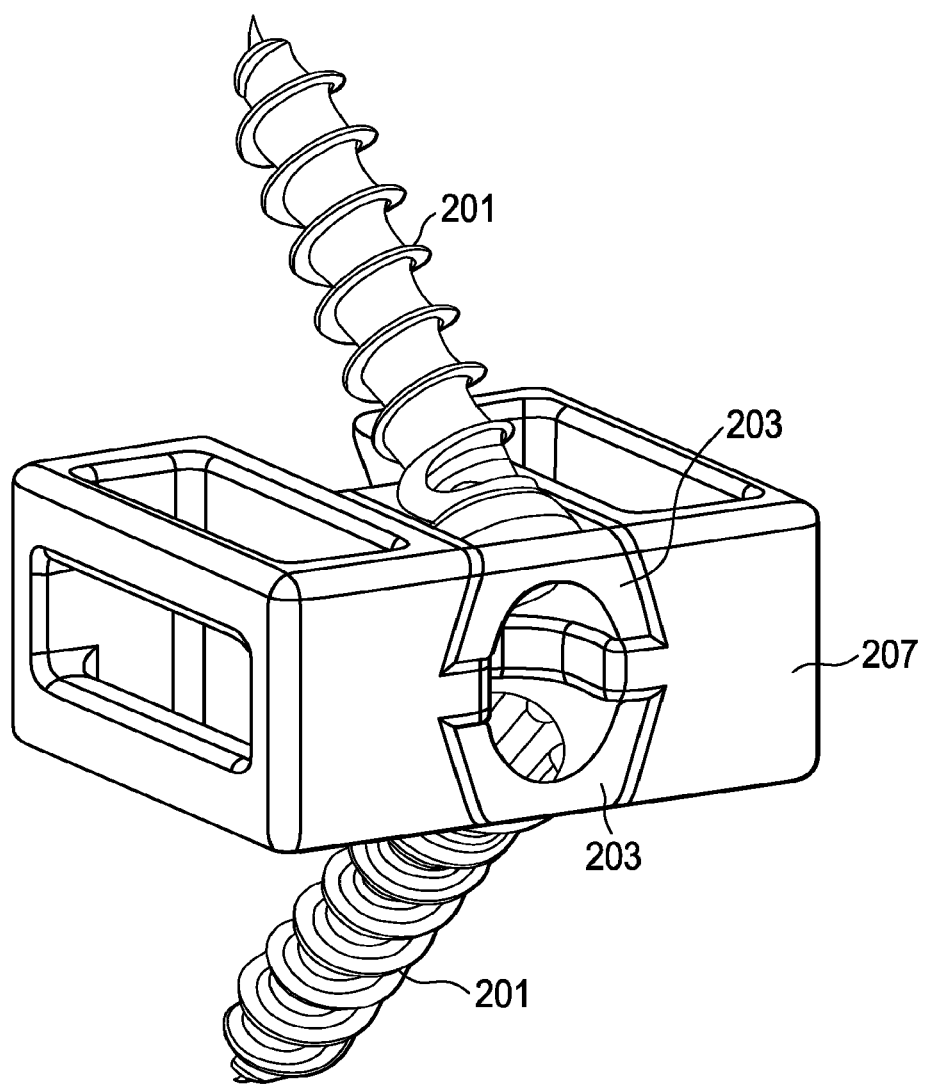
FIG. 12 discloses the assembly comprising the components of FIGS. 13 and 14.
Figure 13:
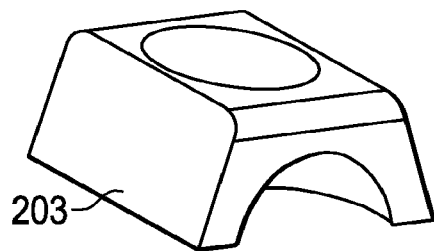
FIG. 13 discloses a second component of the rail-based device of the present invention.
Figure 14:
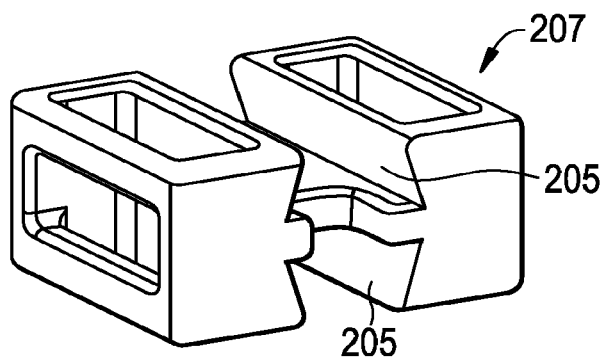
FIG. 14 discloses a first component of the rail-based device of the present invention.

FIGS. 12-14 show another embodiment of this invention. In this embodiment, a sliding component comprises a screw 201 and a rail component 203. Each screw 201 is inserted into its respective endplates along with a rail component 203. The rail component has a cross-section configured to slidingly engage a mating canal in the main interbody device. In this exemplary embodiment, both the rail and the guide surface canal 205 of the main interbody device 207 have dovetail engagement features, although other reliable locking configurations may be used. The advantage of the rail lies in its ability to accommodate variable screw trajectories without the need for a spherical head to ensure alignment with the interbody device. Generally, the rail must be implanted first to envelop the screws, with the screws partially tightened. Then, after sliding the interbody device over the rails, the screws are finally tightened, thereby making the whole construct rigid and properly attached to the vertebrae. The cage may be locked to the rails by the small springy or bump-like feature (not shown) incorporated into the rail and cage design. Preferably, the head of the screw seats on the inner wall of the dovetail canal, thereby preventing the screw from backing out.

Revision surgery can be performed by loosening the screws and removing the cage. In effect, the screws do not need to be removed during cage revision.

Figure 15A:
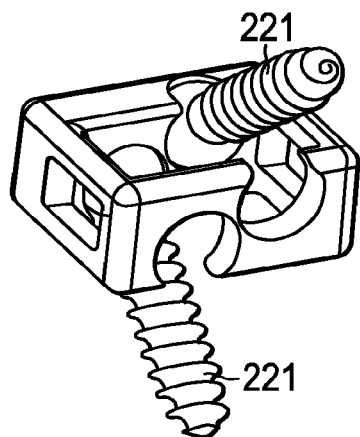
FIGS. 15*a*-15*b* disclose another embodiment of the present invention.
Figure 15B:
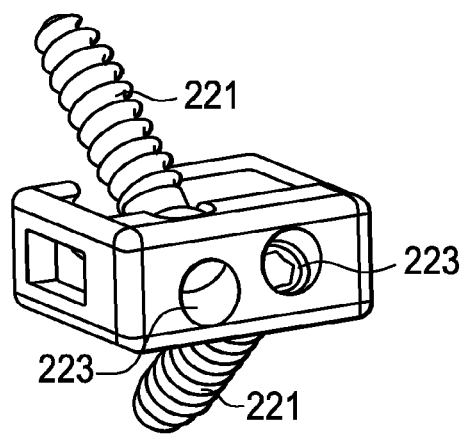

FIGS. 15a and 15b show another embodiment with a pair of screws 221 placed to either side of cage midline. The cage is implanted by sliding the screw heads into the canals of the cage. The final tightening of the screws may be accomplished through the holes 223 provided on the cage's proximal wall after the cage is put in place. The holes have a smaller diameter than the screw head and provide access for a screwdriver shaft while preventing screw backout. The cage is locked in place by the screws' tension, though an additional feature in the form of a small bump (not shown) can be added to prevent cage expulsion. An injectable bone graft or substitute can be injected through the cage side window after final cage assembly. Alternatively, a bone graft substitute such as TCP may be incorporated into the graft at the situs of manufacture.

Figure 16:
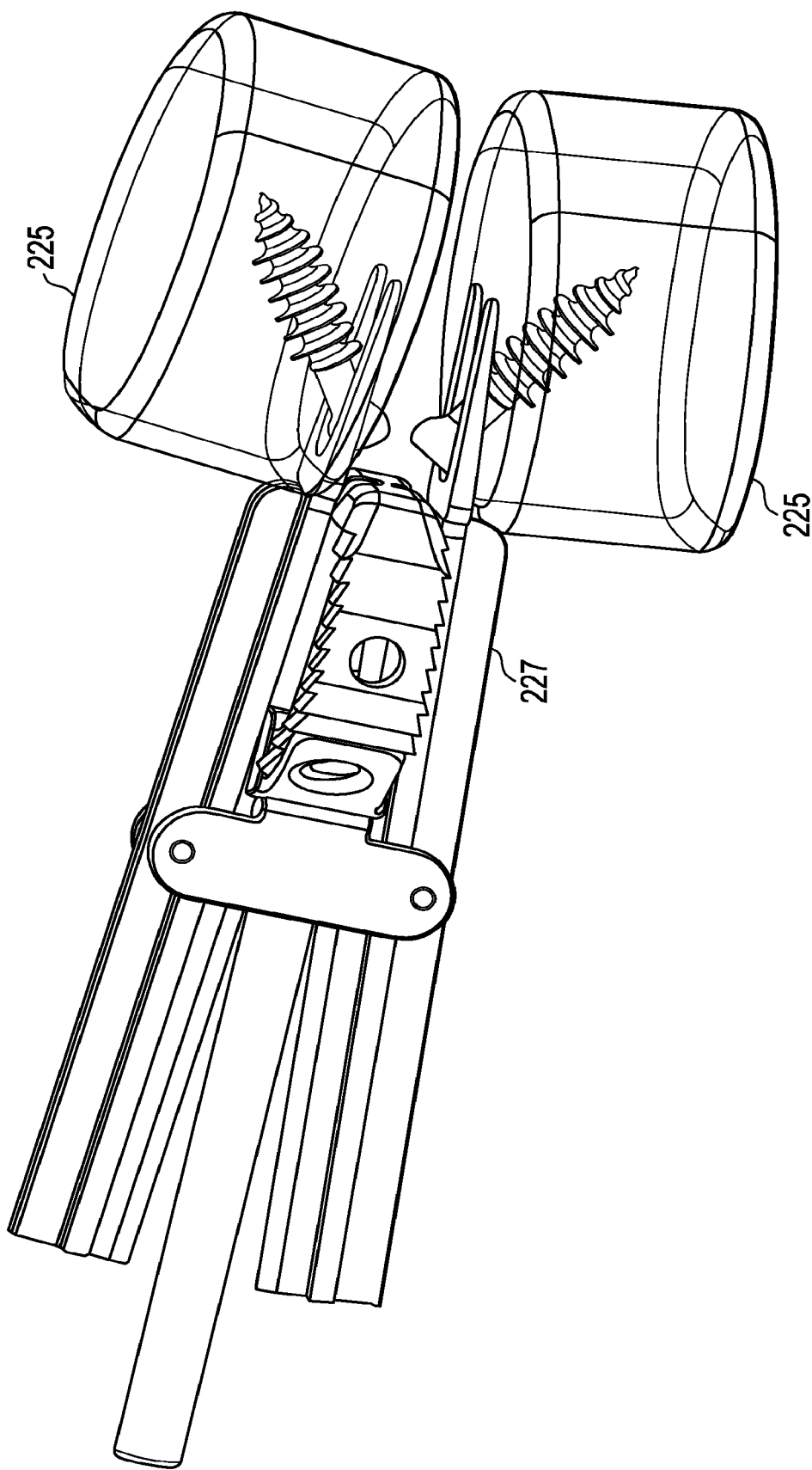
FIG. 16 shows the device of the present invention being implanted into a disc space with a fusion cage inserter.

FIG. 16 shows the device of the present invention being implanted into a disc space with a fusion cage inserter. The screws 225 are held in place on tynes distal of the device of the present invention, and are inserted into the vertebral endplate portion of the disc space so that substantially only their heads protrude from those endplates. Next, the device 227 is slid over the screw heads and is locked in place.

Now referring to FIGS. 18a-18d, a preferred inserter for inserting the present invention comprises a body 103, two blades 105 attached to the body, a pusher 107 attached to the shaft 109 and a handle 111 attached to the shaft.

To implant the cage, the surgeon has to spread the blades and insert the cage in between the blades, aligning the cage's proximal opening with the pusher pin 112. The cage has to be positioned along the inserter so that the pedals are reasonably collapsed in order to be inserted into intervertebral space. The central slots 113 of the blades need to be aligned with the already-implanted screw heads, and the inserter needs to be as vertical as possible (i.e., perpendicular to the anterior plane of the vertebrae) and inserted as deep as the blades' stop surfaces 114 will allow. At this point, the inserter handle is turned clockwise, thereby pushing the pusher and the cage forward. During insertion, pedals 115 become distracted, thereby making space for the cage. The cage is pushed into the disc space until the pusher "stops" contacting the vertebrae. The cage stops advancing forward and the blades withdraw from the disc space by continuing advance of the pusher until the blades are completely withdrawn.

The pusher blade 119 rides inside the pusher guiding slot 117, thereby preventing the pusher from spinning and aligning it properly to the blades. An impactor (not shown) is then used to advance the cage into the final position. At this point, the screw heads serve as stops for the impactor, and the cage cannot move any further distally. At this point, the anterior surface of the cage is flush with the screw heads' most protruding points. The final step is the tightening of the screws.

In some embodiments of the present invention, trialing occurs before implantation of the fusion cage. In particular, in accordance with the present invention, there is provided a method of inserting a fusion cage into an intervertebral disc space formed by upper and lower vertebral endplates, comprising the sequential steps of:

a) inserting a trial having a guide surface canal into the disc space,
b) drilling or awling the hole through the trial drill guides,
c) inserting first and second sliding components into the upper and lower vertebral endplates, the first sliding component having a threaded shank and a screw head,
d) removing the trial,
e) inserting a fusion cage having a guide surface canal into the disc space so that the screw head is received in a distal portion of the canal, and
f) distally translating the cage into the disc space so that the screw head becomes received in a proximal portion of the cage canal.

These cages of the present invention may be made from any non-resorbable material appropriate for human surgical implantation, including but not limited to, surgically appropriate metals, and non-metallic materials, such as carbon fiber composites, polymers and ceramics.

The interbody device and bone anchors are preferably made out of PEEK or CFRP or any other suitable material providing adequate strength and radiolucency. However, implantable metals such as titanium or stainless steel components may be required to ensure adequate strength for either the interbody device or bone anchors. In some cases the interbody device can be made as a combination of PEEK and metal. The metal component is preferably used for screw head retaining feature. In some cases, resorbable materials such as polylactide, polyglycolide, and magnesium are preferred.

In some embodiments, the cage material is selected from the group consisting of PEEK, ceramic and metallic. The cage material is preferably selected from the group consisting of metal and composite (such as PEEK/carbon fiber).

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; polyphenylene and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

In some embodiments, the cage member comprises PEEK. In others, it is a ceramic.

In some embodiments, the first component consists essentially of a metallic material, preferably a titanium alloy or a chrome-cobalt alloy. In some embodiments, the second component consists essentially of the same metallic material as the first plate.

In some embodiments, the components are made of a stainless steel alloy, preferably BioDur® CCM Plus® Alloy available from Carpenter Specialty Alloys, Carpenter Technology Corporation of Wyomissing, Pa. In some embodiments, the outer surfaces of the components are coated with a sintered beadcoating, preferably Porocoat™, available from DePuy Orthopaedics of Warsaw, Ind.

In some embodiments, the components are made from a composite comprising carbon fiber. Composites comprising carbon fiber are advantageous in that they typically have a strength and stiffness that is superior to neat polymer materials such as a polyarylethyl ketone PAEK. In some embodiments, each component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:

a) 40-99% (more preferably, 60-80 vol %) polyarylethyl ketone (PAEK), and
b) 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

Although the present invention has been described with reference to its preferred embodiments, those skillful in the art will recognize changes that may be made in form and structure which do not depart from the spirit of the invention.

Alternatively, combinations of cage materials could be beneficial (i.e., —a ceramic bottom half with a PEEK top half).

In other embodiments, the components are made from resorbable materials, such as Biocryl Rapide™, a PLA, PLG, TCP composite marketed by DePuy Mitek, located in Raynham, Mass.

When resorbable materials are selected, Preferred bioresorbable materials which can be used to make the sutures of the present invention include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates). Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

A variety of bioabsorbable polymers can be used to make the suture of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone(1,4-dioxan-2-one), trimethylene carbonate(1,3-dioxan-2-one), alkyl derivatives of trimethylene carbonate, δ-valerolactone, β-butyrolactone, χ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, χ,χ-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the Handbook of Biodegradable Polymers, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in Handbook of Biodegradable Polymers, edited by Domb, et al, Hardwood Academic Press, pp. 99-118 (1997).

Advantages of the present invention include an ability to have a larger screw diameters. There is no need for a special screw locking mechanism. The screws are locked by the cage design, following a "screw first" concept. There is high reliability in the screw lock. The cage features screw dynamism, so that there is angle flexibility and no bending stress (tension only). The cage allows screw self-adjustment to the cage. The cage may have centrally aligned screws, so there is less risk to veins and arteries. The cage is strongly resistant to axial impact during insertion. The screws are closer to the anterior edge. Lastly, there is a possibility of reducing spondylothesis anteriorly.

What is claimed is:

1. An intervertebral implant configured to be inserted into an intervertebral space defined by a superior vertebra and an inferior vertebra, the intervertebral implant comprising:
    a proximal end and a distal end spaced from one another along a first direction, the proximal end defining a bone screw aperture that extends therethrough, the bone screw aperture configured to receive a bone screw and direct the bone screw into a first one of the superior vertebra and the inferior vertebra;
    first and second sidewalls spaced from one another along a second direction, perpendicular to the first direction, the first and second sidewalls extending from the proximal end to the distal end, each of the first and second sidewalls including an upper bearing surface configured to grip the superior vertebra and a lower bearing surface configured to grip the inferior vertebra, the upper bearing surfaces of the first and second side walls cooperating to define an upper opening configured to promote bony fusion, and the lower bearing surfaces of the first and second side walls cooperating to define a lower opening configured to promote bony fusion;
    a central strut that extends from the distal end toward the proximal end along a centerline of the intervertebral implant such that the central strut is elongate along the first direction, the central strut having at least one guiding surface that extends along the first direction; and
    at least one sliding component configured to ride along the at least one guiding surface of the central strut along the first direction, wherein the at least one sliding component comprises a threaded shank that is configured to be anchored in a second one of the superior vertebra and the inferior vertebra.

2. The intervertebral implant of claim 1, wherein the proximal end, the central strut and the distal end are unitary.

3. The intervertebral implant of claim 1, wherein the central strut is disposed between the first and second sidewalls with respect to the second direction.

4. The intervertebral implant of claim 1, wherein the implant defines first and second apertures that extends through the implant from the upper opening to the lower opening along a third direction, perpendicular to both the first and second directions, the first and second apertures configured to promote bony fusion.

5. The intervertebral implant of claim 4, wherein the first aperture extends from the upper bearing surface of the first sidewall to the lower bearing surface of the first sidewall, and the second aperture extends from the upper bearing surface of the second sidewall to the lower bearing surface of the second sidewall.

6. The intervertebral implant of claim 4, wherein the central strut is disposed between the first and second apertures.

7. The intervertebral implant of claim 6, wherein the first aperture extends from the central strut to the first sidewall along the second direction, and the second aperture extends from the central strut to the second sidewall along the second direction.

8. The intervertebral implant of claim 1, wherein the upper bearing surfaces and the lower bearing surfaces of the first and second sidewalls each include a plurality of teeth configured to engage bone.

9. The intervertebral implant of claim 1, wherein the at least one guiding surface includes a first guiding surface defined on an upper portion of the central strut and a second guiding surface defined on a lower portion of the central strut.

10. The intervertebral implant of claim 9, wherein the first guiding surface and the second guiding surface are spaced from on another along a third direction, perpendicular to both the first and second directions.

11. The intervertebral implant of claim 1, wherein each of the first and second sidewalls is configured to attach to the proximal end and the distal end.

12. The intervertebral implant of claim 1, wherein the at least one sliding component is configured to be anchored to the second one of the superior and inferior vertebra when the at least one sliding component is received by the central strut.

13. The intervertebral implant of claim 1, wherein the threaded shank is a first threaded shank, and the at least one sliding component comprises a second threaded shank configured to be anchored in one of the superior vertebra and the inferior vertebra.

14. An intervertebral system, comprising the intervertebral implant of claim 13 and a bone screw configured to extend through the bone screw aperture and into the one of the superior and inferior vertebra.

15. The intervertebral system of claim 14, wherein the bone screw is a first bone screw, the bone screw aperture is a first bone screw aperture, the proximal end defines a second bone screw aperture that extends therethrough the proximal end and defines a second bone screw aperture that extends therethrough, and the intervertebral system comprises a second bone screw configured to extend through the second bone screw aperture and into one of the superior and inferior vertebra.

16. An intervertebral system comprising the intervertebral implant of claim 1 and a bone screw configured to extend through the bone screw aperture and into the first one of the superior and inferior vertebra.

17. The intervertebral system of claim 16, wherein the bone screw is a first bone screw, the bone screw aperture is a first bone screw aperture, the proximal end defines a second bone screw aperture that extends therethrough, and the intervertebral system comprises a second bone screw configured to extend through the second bone screw aperture and into one of the superior and inferior vertebra.

18. The intervertebral implant of claim 1, wherein the at least one sliding component comprises at least one sliding surface that is configured to slide along the at least one guiding surface of the central strut along the first direction.

19. The intervertebral implant of claim 18, wherein the at least one sliding component is configured to slide along the at least one guiding surface without rotating.

20. The intervertebral implant of claim 1, wherein the at least one sliding component is configured to ride along at least a midpoint of the at least one guide surface of the central strut that is midway between the proximal and distal ends.

* * * * *